US011078215B2

(12) United States Patent
Pencheva

(10) Patent No.: US 11,078,215 B2
(45) Date of Patent: Aug. 3, 2021

(54) CRYSTALLINE FORMS OF LORLATINIB MALEATE

(71) Applicant: Pfizer Inc., New York, NY (US)

(72) Inventor: Klimentina Dimitrova Pencheva, Ramsgate (GB)

(73) Assignee: Pfizer Inc., New York, NY (US)

( * ) Notice: Subject to any disclaimer, the term of this patent is extended or adjusted under 35 U.S.C. 154(b) by 199 days.

(21) Appl. No.: 16/090,693

(22) PCT Filed: Mar. 27, 2017

(86) PCT No.: PCT/IB2017/051739
§ 371 (c)(1),
(2) Date: Oct. 2, 2018

(87) PCT Pub. No.: WO2017/175091
PCT Pub. Date: Oct. 12, 2017

(65) Prior Publication Data
US 2020/0325155 A1  Oct. 15, 2020

Related U.S. Application Data
(60) Provisional application No. 62/320,305, filed on Apr. 8, 2016.

(51) Int. Cl.
*C07D 498/18* (2006.01)
(52) U.S. Cl.
CPC ........ *C07D 498/18* (2013.01); *C07B 2200/13* (2013.01)
(58) Field of Classification Search
CPC .................................................. C07D 498/18
USPC ........................................................ 514/286
See application file for complete search history.

(56) References Cited

U.S. PATENT DOCUMENTS

| 8,680,111 | B2 * | 3/2014 | Bailey | C07D 513/18 |
| | | | | 514/286 |
| 8,916,593 | B2 | 12/2014 | Bunnage et al. | |
| 9,133,215 | B2 | 6/2015 | Bailey et al. | |
| 9,637,500 | B2 | 5/2017 | Jensen et al. | |
| 10,420,749 | B2 * | 9/2019 | Pencheva | A61K 31/4162 |
| 2018/0235933 | A1 | 8/2018 | Pencheva et al. | |

FOREIGN PATENT DOCUMENTS

| WO | 2013132376 | 9/2013 |
| WO | 2014207606 | 12/2014 |
| WO | 2017021823 | 2/2017 |
| WO | 2017175091 | 10/2017 |
| WO | 2019073347 | 4/2019 |

OTHER PUBLICATIONS

U.S. Appl. No. 15/743,894, filed Jul. 27, 2016.
Awad et al., "Acquired Resistance to Crizotinib from a Mutation in CD74-ROS1." N Engl J Med 2013; 368:2395-2401.
Birchmeier et al. "Expression and rearrangement of the ROSI gene in human glioblastoma cells." Proc Natl Acad Sci 1987; 84:9270-9274.
Birchmeier et al., "Characterization of an Activated Human ros Gene." Mol. Cell. Bio. 1986; 6(9):3109-3115.
Caren et al., "High incidence of DNA mutations and gene amplifications of the ALK gene in advanced sporadic neuroblastoma tumors." Biochem. J. 2008; 416:153-159.
Charest et al., "Fusion of FIG to the Receptor Tyrosine Kinase ROS in a Glioblastoma with an Interstitial del(6) (q21q21)." Genes Chromos. Can. 2003; 37(1): 58-71.
Choi et al., "EML4-ALK Mutations in Lung Cancer than Confer Resistance to ALK Inhibitors." N Engl J Med 2010; 363:1734-1739.
Gschwind et al., "The discovery of receptor tyrosine kinases: targets for cancer therapy." Nat. Rev. Cancer 2004; 4, 361-370.
Gu et al. "Survey of Tyrosine Kinase Signaling Reveals ROS Kinase Fusions in Human Cholangiocarcinoma." PLoS One 2011; 6(1): e15640.
Hanahan & Weinberg, "The hallmarks of cancer." Cell 2000; 100: 57-70.
International Preliminary Report on Patentability dated Oct. 9, 2018 for International Publication No. WO 2017175091.
International Search Report completed on May 9, 2017 for International Publication No. WO 2017175091.
Johnson et al., "Discovery of (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a Macrocyclic Inhibitor of Anaplastic Lymphoma Kinase (ALK) and c-ros Oncogene 1 (ROS1) with Preclinical Brain Exposure and Broad-Spectrum Potency against ALK-Resistant Mutations" J. Med. Chem. 2014, 57:4720-4744.
Krause & Van Et-ten, "Tyrosine kinases as targets for cancer therapy." N. Engl. J. Med. 2005; 353: 172-187.
Morris et al., "Fusion of a kinase gene, ALK, to a nucleolar protein gene, NPM, in non-Hodgkin's lymphoma." Science 1994; 263:1281-1284.
Nagarajan et al. "The human c-ros gene (ROS) is located at chromosome region 6q166q22." Proc Natl Acad Sci 1986; 83:6568-6572.
Palmer et al., "Anaplastic lymphoma kinase: signaling in development and disease." Biochem. J. 2009; 420:345-361.
Pulford et al., "Anaplastic lymphoma kinase proteins in growth control and cancer." J. Cell Physiol., 2004; 199: 330-58.
Rikova et al., "Global Survey of Phosphotyrosine Signaling Identifies Oncogenic Kinases in Lung Cancer." Cell 2007; 131:1190-1203.

(Continued)

*Primary Examiner* — Nizal S Chandrakumar
(74) *Attorney, Agent, or Firm* — Fariba Shoarinejad

(57) ABSTRACT

This invention relates to new crystalline forms of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile(lorlatinib) maleate. The invention also relates to pharmaceutical compositions comprising lorlatinib maleate, and to methods of using lorlatinib maleate and compositions comprising it in the treatment of abnormal cell growth, such as cancer, in mammals.

21 Claims, 10 Drawing Sheets

(56) References Cited

OTHER PUBLICATIONS

Rimkunas et al., "Analysis of Receptor Tyrosine Kinase ROS1-Positive Tumors in Non-Small Cell Lung Cancer: Identification of FIG-ROS1 Fusion." Clin Cancer Res 2012; 18:4449-4457.
Shaw et al. "Clinical activity of crizotinib in advanced non-small cell lung cancer (NSCLC) harboring ROS1 gene rearrangement." Presented at the Annual Meeting of the American Society of Clinical Oncology, Chicago, Jun. 1-5, 2012.
Soda et al., "Identification of the transforming EML4-ALK fusion gene in non-small cell lung cancer." Nature 2007; 448:561-566.
Soda et al., "A mouse model for EML4-ALK-positive lung cancer." Proc. Natl. Acad. Sci. U.S.A. 2008; 105:19893-19897.
Takeuchi et al., "RET, ROS1 and ALK fusions in lung cancer." Nature Medicine 2012; 18(3):378-381).
Wan et al., "Anaplastic lymphoma kinase activity is essential for the proliferation and survival of anaplastic large cell lymphoma cells." Blood, 2006; 107:1617-1623.
Written Opinion of the International Searching Authority dated Oct. 12, 2017 for International Publication No. WO 2017175091.
Byrn, S., et al., "Pharmaceutical Solids: A Strategic Approach to Regulatory Considerations", Pharm Research, 1995, pp. 945-954, vol. 12, No. 7.
Khankari, R., et al., "Pharmaceutical Hydrates", Thermochimica Acta, 1995, p. 61-79, vol. 248.
EPO Search Report, completion dated Oct. 29, 2020, EP20190143.

\* cited by examiner

CRYSTALLINE FORMS OF LORLATINIB MALEATE

CROSS-REFERENCE TO RELATED APPLICATIONS

This Application is the national stage filing under 35 U.S.C. 371 of Patent Cooperation Treaty Patent Application No. PCT/IB2017/051739, filed Mar. 27, 2017, which claims the benefit of priority from U.S. Provisional Application No. 62/320,305 filed Apr. 8, 2016, the contents of each of which are hereby incorporated by reference in their entireties.

FIELD OF THE INVENTION

This invention relates to new crystalline forms of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile maleate (lorlatinib maleate), to pharmaceutical compositions comprising lorlatinib maleate, and to methods of using lorlatinib maleate and compositions comprising it in the treatment of abnormal cell growth, such as cancer, in mammals.

BACKGROUND OF THE INVENTION

The compound (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (PF-06463922), represented by the formula (I):

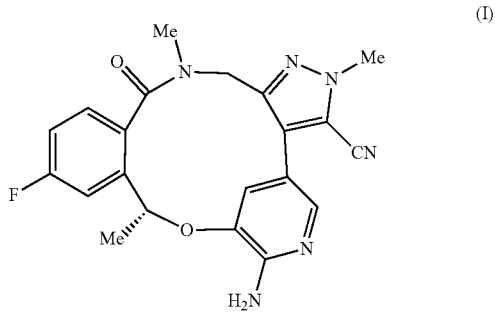 [SMILES: C[C@H]1Oc2cc(cnc2N)-c2c(nn(C)c2C#N)CN(C)C(=O)c2ccc(F)cc21]

(I)

has been assigned the International Nonproprietary Name (INN) lorlatinib, as described in *WHO Drug Information*, Vol. 29, No. 4, page 541 (2015). Lorlatinib is a potent, macrocyclic inhibitor of both wild type and resistance mutant forms of anaplastic lymphoma kinase (ALK) and c-ros oncogene 1 (ROS1) receptor tyrosine kinase. The maleate salt of Formula (I) may also be referred to herein as (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile maleate or lorlatinib maleate.

Preparation of the free base of lorlatinib as an amorphous solid is disclosed in International Patent Publication No. WO 2013/132376 and in U.S. Pat. No. 8,680,111. Solvated forms of lorlatinib free base are disclosed in International Patent Publication No. WO 2014/207606. Preparation of an anhydrous crystalline form of lorlatinib free base is disclosed in International Application No. PCT/IB2016/054483. The contents of each of the foregoing documents are incorporated herein by reference in their entirety.

Human cancers comprise a diverse array of diseases that collectively are one of the leading causes of death in developed countries throughout the world (American Cancer Society, Cancer Facts and Figures 2005. Atlanta: American Cancer Society; 2005). The progression of cancers is caused by a complex series of multiple genetic and molecular events including gene mutations, chromosomal translocations and karyotypic abnormalities (Hanahan & Weinberg. The hallmarks of cancer. Cell 2000; 100: 57-70). Although the underlying genetic causes of cancer are both diverse and complex, each cancer type has been observed to exhibit common traits and acquired capabilities that facilitate its progression. These acquired capabilities include dysregulated cell growth, sustained ability to recruit blood vessels (i.e., angiogenesis) and ability of tumor cells to spread locally as well as metastasize to secondary organ sites (Hanahan & Weinberg 2000). Therefore, the ability to identify novel therapeutic agents that inhibit molecular targets that are altered during cancer progression or target multiple processes that are common to cancer progression in a variety of tumors presents a significant unmet need.

Receptor tyrosine kinases (RTKs) play fundamental roles in cellular processes, including cell proliferation, migration, metabolism, differentiation and survival. RTK activity is tightly controlled in normal cells. The constitutively enhanced RTK activities from point mutation, amplification and rearrangement of the corresponding genes have been implicated in the development and progression of many types of cancer. (Gschwind et al., The discovery of receptor tyrosine kinases: targets for cancer therapy. Nat. Rev. Cancer 2004; 4, 361-370; Krause & Van Etten, Tyrosine kinases as targets for cancer therapy. N. Engl. J. Med. 2005; 353: 172-187.)

Anaplastic lymphoma kinase (ALK) is a receptor tyrosine kinase, grouped together with leukocyte tyrosine kinase (LTK) to a subfamily within the insulin receptor (IR) superfamily. ALK was first discovered as a fusion protein with nucleophosmin (NPM) in anaplastic large cell lymphoma (ALCL) cell lines in 1994. (Morris et al., Fusion of a kinase gene, ALK, to a nucleolar protein gene, NPM, in non-Hodgkin's lymphoma. Science 1994; 263:1281-1284.) NPM-ALK, which results from a chromosomal translocation, is implicated in the pathogenesis of human anaplastic large cell lymphoma (ALCL) (Pulford et al., Anaplastic lymphoma kinase proteins in growth control and cancer. J. Cell Physiol., 2004; 199: 330-58). The roles of aberrant expression of constitutively active ALK chimeric proteins in the pathogenesis of ALCL have been defined (Wan et. al., Anaplastic lymphoma kinase activity is essential for the proliferation and survival of anaplastic large cell lymphoma cells. Blood, 2006; 107:1617-1623). Other chromosomal rearrangements resulting in ALK fusions have been subsequently detected in ALCL (50-60%), inflammatory myofibroblastic tumors (27%) and non-small-cell lung cancer (NSCLC) (2-7%). (Palmer et al., Anaplastic lymphoma kinase: signaling in development and disease. Biochem. J. 2009; 420:345-361.)

The EML4-ALK fusion gene, comprising portions of the echinoderm microtubule associated protein-like 4 (EML4) gene and the ALK gene, was first discovered in NSCLC archived clinical specimens and cell lines. (Soda et al., Identification of the transforming EML4-ALK fusion gene in non-small cell lung cancer. Nature 2007; 448:561-566; Rikova et al., Cell 2007; 131:1190-1203.) EML4-ALK fusion variants were demonstrated to transform NIH-3T3 fibroblasts and cause lung adenocarcinoma when expressed in transgenic mice, confirming the potent oncogenic activity of the EML4-ALK fusion kinase. (Soda et al., A mouse model for EML4-ALK-positive lung cancer. Proc. Natl. Acad. Sci. U.S.A. 2008; 105:19893-19897.) Oncogenic mutations of ALK in both familial and sporadic cases of neuroblastoma have also been reported. (Caren et al., High incidence of DNA mutations and gene amplifications of the ALK gene in advanced sporadic neuroblastoma tumors. Biochem. J. 2008; 416:153-159.)

ROS1 is a proto-oncogene receptor tyrosine kinase that belongs to the insulin receptor subfamily and is involved in cell proliferation and differentiation processes. (Nagarajan et al. Proc Natl Acad Sci 1986; 83:6568-6572). ROS1 is expressed, in humans, in epithelial cells of a variety of different tissues. Defects in ROS1 expression and/or activation have been found in glioblastoma, as well as tumors of the central nervous system (Charest et al., Genes Chromos. Can. 2003; 37(1): 58-71). Genetic alterations involving ROS1 that result in aberrant fusion proteins of ROS1 kinase have been described, including the FIG-ROS1 deletion translocation in glioblastoma (Charest et al. (2003); Birchmeier et al. Proc Natl Acad Sci 1987; 84:9270-9274; and NSCLC (Rimkunas et al., Analysis of Receptor Tyrosine Kinase ROS1-Positive Tumors in Non-Small Cell Lung Cancer: Identification of FIG-ROS1 Fusion, Clin Cancer Res 2012; 18:4449-4457), the SLC34A2-ROS1 translocation in NSCLC (Rikova et al. Cell 2007; 131:1190-1203), the CD74-ROS1 translocation in NSCLC (Rikova et al. (2007)) and cholangiocarcinoma (Gu et al. PLoS ONE 2011; 6(1): e15640) and a truncated, active form of ROS1 known to drive tumor growth in mice (Birchmeier et al. Mol. Cell. Bio. 1986; 6(9):3109-3115). Additional fusions, including TPM3-ROS1, SDC4-ROS1, EZR-ROS1 and LRIG3-ROS1, have been reported in lung cancer patient tumor samples (Takeuchi et al., RET, ROS1 and ALK fusions in lung cancer, Nature Medicine 2012; 18(3):378-381).

The ALK/ROS1/c-MET inhibitor crizotinib was approved in 2011 for the treatment of patients with locally advanced or metastatic NSCLC that is ALK-positive as detected by an FDA-approved test. Crizotinib has also shown efficacy in treatment of NSCLC with ROS1 translocations. (Shaw et al. Clinical activity of crizotinib in advanced non-small cell lung cancer (NSCLC) harboring ROS1 gene rearrangement. Presented at the Annual Meeting of the American Society of Clinical Oncology, Chicago, Jun. 1-5, 2012.) As observed clinically for other tyrosine kinase inhibitors, mutations in ALK and ROS1 that confer resistance to ALK inhibitors have been described (Choi et al., EML4-ALK Mutations in Lung Cancer than Confer Resistance to ALK Inhibitors, N Engl J Med 2010; 363:1734-1739; Awad et al., Acquired Resistance to Crizotinib from a Mutation in CD74-ROS1, N Engl J Med 2013; 368:2395-2401).

Thus, ALK and ROS1 are attractive molecular targets for cancer therapeutic intervention. There remains a need to identify compounds having novel activity profiles against wild-type and mutant forms of ALK and ROS1.

The present invention provides novel crystalline forms of lorlatinib maleate having desirable properties, such as high crystallinity, high purity, low hygroscopicity and favorable dissolution and mechanical properties. In particular, lorlatinib maleate hydrate provides improved physical stability in the drug product formulation relative to the acetic acid solvate form disclosed in International Patent Publication No. WO 2014/207606. Such solvated forms may present challenges for drug development, in particular with respect to physical stability. Consequently, there remains a need to identify novel forms having desirable physicochemical properties.

SUMMARY OF THE INVENTION

In a first aspect, the invention provides a crystalline form of lorlatinib maleate hydrate (Form 2), which is characterized by one or more of the following methods: (1) powder X-ray diffraction (PXRD) (2θ); (2) Raman spectroscopy (cm$^{-1}$); (3) $^{13}$C solid state NMR spectroscopy (ppm); or (4) $^{19}$F solid state NMR spectroscopy (ppm).

In some embodiments of the first aspect, the invention provides lorlatinib maleate hydrate (Form 2), which is characterized as having:

(1) a powder X-ray diffraction (PXRD) pattern (2θ) comprising: (a) one, two, three, four, five, or more than five peaks selected from the group consisting of the peaks in Table 1 in °2θ±0.2°2θ; (b) one, two, three, four or five peaks selected from the group consisting of the characteristic peaks in Table 1 in °2θ±0.2°2θ; or (c) peaks at 2θ values essentially the same as shown in FIG. 1; or (2) a Raman spectrum comprising: (a) one, two, three, four, five, or more than five wavenumber (cm$^{-1}$) values selected from the group consisting of the values in Table 2 in cm$^{-1}$±2 cm$^{-1}$; (b) one, two, three, four, five, or more than five wavenumber (cm$^{-1}$) values selected from the group consisting of the characteristic values in Table 2 in cm$^{-1}$±2 cm$^{-1}$; or (c) wavenumber (cm$^{-1}$) values essentially the same as shown in FIG. 2; or (3) a $^{13}$C solid state NMR spectrum (ppm) comprising: (a) one, two, three, four, five, or more than five resonance (ppm) values selected from the group consisting of the values in Table 3 in ppm±0.2 ppm; (b) one, two, three or four resonance (ppm) values selected from the group consisting of the characteristic values in Table 3 in ppm±0.2 ppm; or (c) resonance (ppm) values essentially the same as shown in FIG. 3; or (4) a $^{19}$F solid state NMR spectrum (ppm) comprising: (a) the resonance (ppm) value in Table 4 in ppm±0.2 ppm; or (b) resonance (ppm) values essentially the same as shown in FIG. 4;

or a combination of any two, three or four of the foregoing embodiments (1)(a)-(c), (2)(a)-(c), (3)(a)-(c), or (4)(a)-(b), provided they are not inconsistent with each other.

In a second aspect, the invention provides a crystalline anhydrous lorlatinib maleate (Form 1), which is characterized by one or more of the following methods: (1) powder X-ray diffraction (PXRD) (2θ); (2) Raman spectroscopy (cm$^{-1}$); (3) $^{13}$C solid state NMR spectroscopy (ppm); or (4) $^{19}$F solid state NMR spectroscopy (ppm).

In some embodiments of this aspect, the invention provides anhydrous lorlatinib maleate (Form 1), which is characterized as having:

(1) a powder X-ray diffraction (PXRD) pattern (2θ) comprising: (a) one, two, three four, five, or more than five peaks selected from the group consisting of the peaks in Table 5 in °2θ±0.2°2θ; (b) one, two, three or four peaks selected from the group consisting of the characteristic peaks in Table 5 in °2θ±0.2°2θ; or (c) peaks at 2θ values essentially the same as shown in FIG. 5; or (2) a Raman spectrum comprising: (a) one, two, three, four, five, or more than five wavenumber (cm$^{-1}$) values selected from the group consisting of the values in Table 6 in cm$^{-1}$±2 cm$^{-1}$; or (b) wavenumber (cm$^{-1}$) values essentially the same as shown in FIG. 6; or (3) a $^{13}$C solid state NMR spectrum (ppm) comprising: (a) one, two, three, four, five, or more than five resonance (ppm) values selected from the group consisting of the values in Table 7 in ppm±0.2 ppm; or (b) resonance (ppm) values essentially the same as shown in FIG. 7; or (4) a $^{19}$F solid state NMR spectrum (ppm) comprising: (a) the resonance (ppm) value in Table 8 in ppm±0.2 ppm; or (b) resonance (ppm) values essentially the same as shown in FIG. 8;

or a combination of any two, three or four of the foregoing embodiments (1)(a)-(c), (2)(a)-(b), (3)(a)-(b), or (4)(a)-(b), provided they are not inconsistent with each other.

In a third aspect, the invention provides a pharmaceutical composition comprising lorlatinib maleate, according to any of the embodiments described herein, and a pharmaceutically acceptable carrier or excipient. In some embodiments, the pharmaceutical composition comprises lorlatinib maleate hydrate (Form 2) and a pharmaceutically acceptable carrier or excipient. In other embodiments, the pharmaceutical composition comprises anhydrous lorlatinib maleate (Form 1) and a pharmaceutically acceptable carrier or excipient.

In a fourth aspect, the invention provides use of lorlatinib maleate, or a pharmaceutical composition comprising it, according to any of the aspects or embodiments described herein, for the treatment of abnormal cell growth in a mammal. In some such embodiments, the invention provides the use of lorlatinib maleate hydrate (Form 2). In other embodiments, the invention provides the use of anhydrous lorlatinib maleate (Form 1).

In a fifth aspect, the invention provides use of lorlatinib maleate according to any of the aspects or embodiments described herein, in the manufacture of a medicament for the treatment of abnormal cell growth in a mammal. In some such embodiments, the invention provides the use of lorlatinib maleate hydrate (Form 2) to manufacture a medicament. In other embodiments, the invention provides the use of anhydrous lorlatinib maleate (Form 1) to manufacture a medicament.

In a sixth aspect, the invention provides a method of treating abnormal cell growth, such as cancer, in a mammal, comprising administering to the mammal a therapeutically effective amount of lorlatinib maleate, or a pharmaceutical composition comprising it, according to any of the aspects or embodiments described herein. In some such embodiments, the method comprises administering lorlatinib maleate hydrate (Form 2) to a mammal in need of such treatment. In other embodiments, the method comprises administering anhydrous lorlatinib maleate (Form 1) to a mammal in need of such treatment. In frequent embodiments the mammal is a human.

In frequent embodiments of the aspects described herein, the abnormal cell growth is cancer. In some embodiments, the abnormal cell growth is cancer mediated by ALK or ROS1. In some such embodiments, the abnormal cell growth is cancer mediated by ALK. In other such embodiments, the abnormal cell growth is cancer mediated by ROS1. In further embodiments, the abnormal cell growth is cancer mediated by at least one genetically altered tyrosine kinase, such as a genetically altered ALK or a genetically altered ROS1.

In some such embodiments, the cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma and combinations thereof.

In other such embodiments, the cancer is selected from the group consisting of non-small cell lung cancer (NSCLC), squamous cell carcinoma, hormone-refractory prostate cancer, papillary renal cell carcinoma, colorectal adenocarcinoma, neuroblastoma, anaplastic large cell lymphoma (ALCL) and gastric cancer. In specific embodiments, the cancer is non-small cell lung cancer (NSCLC). In particular embodiments, the cancer is NSCLC mediated by ALK or ROS1 and more particularly, NSCLC mediated by a genetically altered ALK or a genetically altered ROS1.

DETAILED DESCRIPTION OF THE INVENTION

Figure 1:
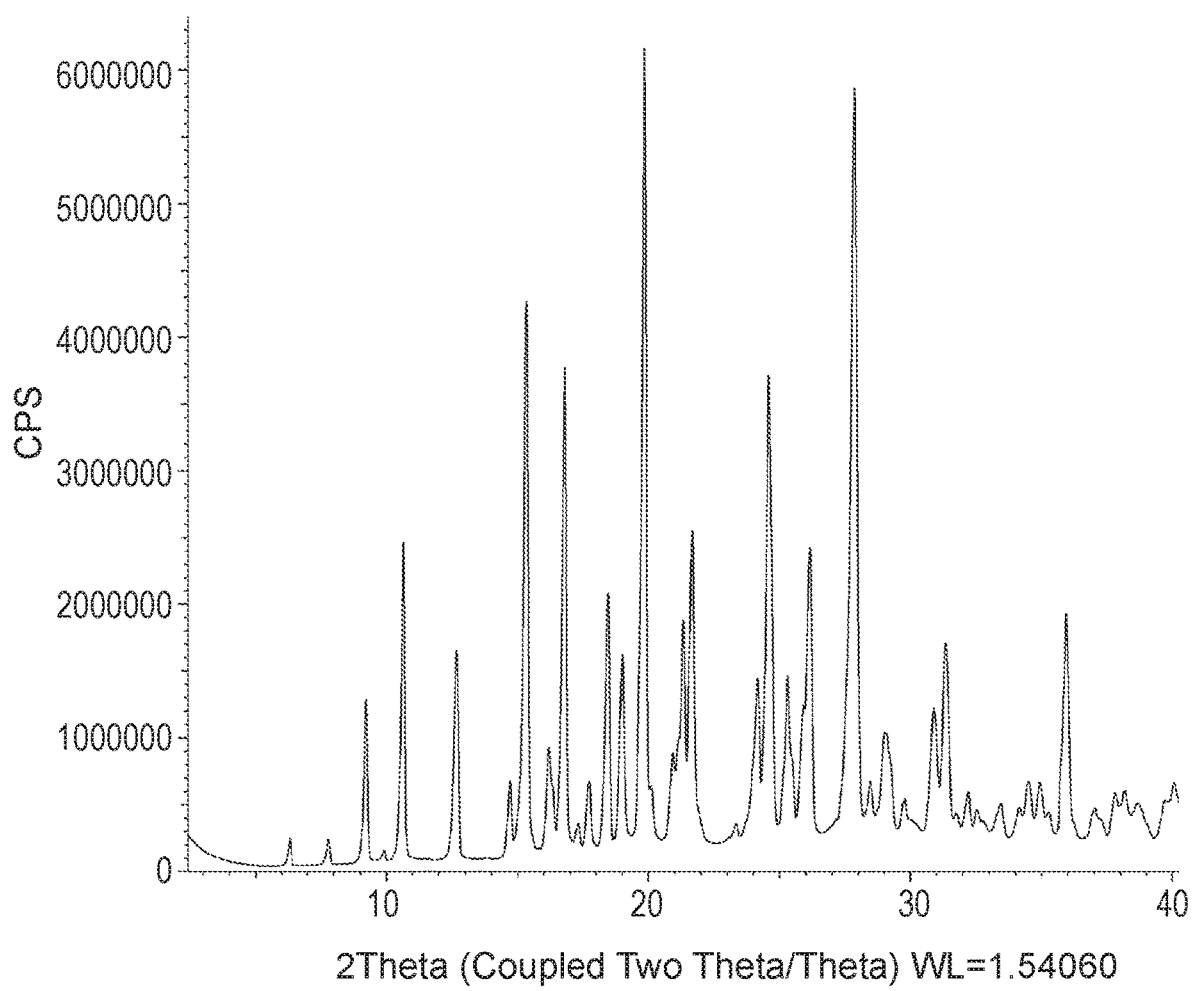
FIG. 1: PXRD pattern of lorlatinib maleate hydrate (Form 2).

The present invention may be understood more readily by reference to the following detailed description of the embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an" and "the" include plural references unless indicated otherwise. For example, "a" substituent includes one or more substituents.

The term "about" means having a value falling within an accepted standard of error of the mean, when considered by one of ordinary skill in the art.

As used herein, the term "essentially the same" means that variability typical for a particular method is taken into account. For example, with reference to X-ray diffraction peak positions, the term "essentially the same" means that typical variability in peak position and intensity are taken into account. One skilled in the art will appreciate that the peak positions (2θ) will show some variability, typically as much as ±0.2°. Further, one skilled in the art will appreciate that relative peak intensities will show inter-apparatus variability as well as variability due to degree of crystallinity, preferred orientation, prepared sample surface and other factors known to those skilled in the art and should be taken as qualitative measures only. Similarly, Raman spectrum wavenumber (cm$^{-1}$) values show variability, typically as much as ±2 cm$^{-1}$, while $^{13}$C and $^{19}$F solid state NMR spectrum (ppm) show variability, typically as much as ±0.2 ppm.

The term "crystalline" as used herein, means having a regularly repeating arrangement of molecules or external face planes. Crystalline forms may differ with respect to thermodynamic stability, physical parameters, x-ray structure and preparation processes.

The term "amorphous" refers to a disordered solid state.

The term "solvate" as used herein, means having on a surface, in a lattice or on a surface and in a lattice, a stoichiometric or non-stoichiometric amount of a solvent such as water, acetic acid, methanol, etc., or mixtures thereof, bound by non-covalent intermolecular forces. The term "hydrate" may be used specifically to describe a solvate comprising water.

The term "anhydrous" as used herein, means a crystalline form containing less than about 1% (w/w) of adsorbed moisture as determined by standard methods, such as a Karl Fisher analysis.

The invention described herein may be suitably practiced in the absence of any element(s) not specifically disclosed herein. Thus, for example, in each instance herein any of the terms "comprising", "consisting essentially of" and "consisting of" may be replaced with either of the other two terms.

In one aspect, the invention provides lorlatinib maleate hydrate (Form 2). As disclosed herein, Form 2 has physical stability, manufacturability and mechanical properties that are favorable for use in pharmaceutical formulations. The methods described herein provide lorlatinib maleate hydrate (Form 2) which is substantially pure and free of alternative forms, including the solvated forms disclosed previously.

As described herein, lorlatinib maleate Form 1 and Form 2 were characterized by PXRD, Raman spectroscopy and $^{13}$C and $^{19}$F solid state NMR spectroscopy. Such crystalline forms may be further characterized by additional techniques, such as Fourier-Transform InfraRed Spectroscopy (FTIR), Differential Scanning Calorimetry (DSC), Thermogravimetric Analysis (TGA) or Differential Thermal Analysis (DTA).

In some embodiments of each of the aspects of the invention, lorlatinib maleate is characterized by its powder X-ray diffraction (PXRD) pattern. In other embodiments of each of the aspects of the invention, lorlatinib maleate is characterized by its Raman spectrum. In other embodiments of each of the aspects of the invention, lorlatinib maleate is characterized by its $^{13}$C solid state NMR spectrum. In still other embodiments of each of the aspects of the invention, lorlatinib maleate is characterized by its $^{19}$F solid state NMR spectrum.

In further embodiments, lorlatinib maleate is characterized by a combination of two, three or four of these methods. Exemplary combinations including two or more of the following are provided herein: powder X-ray diffraction (PXRD) pattern (2θ); Raman spectrum wavenumber values (cm$^{-1}$); $^{13}$C solid state NMR spectrum (ppm); or $^{19}$F solid state NMR spectrum (ppm). It will be understood that other combinations of two, three or four techniques may be used to uniquely characterize lorlatinib maleate disclosed herein.

In a first aspect, the invention provides lorlatinib maleate hydrate (Form 2). In one embodiment, lorlatinib maleate hydrate (Form 2) has a PXRD pattern comprising one or more peaks at 2θ values selected from the group consisting of: 10.6, 12.7, 16.2, 18.5 and 27.8°2θ±0.2°2θ. In another embodiment, lorlatinib maleate hydrate (Form 2) has a PXRD pattern comprising two or more peaks at 2θ values selected from the group consisting of: 10.6, 12.7, 16.2, 18.5 and 27.8°2θ±0.2°2θ. In another embodiment, lorlatinib maleate hydrate (Form 2) has a PXRD pattern comprising three or more peaks at 2θ values selected from the group consisting of: 10.6, 12.7, 16.2, 18.5 and 27.8°2θ±0.2°2θ.

In another embodiment, Form 2 has a PXRD pattern comprising peaks at 2θ values of: 10.6, 18.5 and 27.8°2θ±0.2°2θ. In some such embodiments, Form 2 has a PXRD pattern further comprising a peak at the 2θ value of: 12.7°2θ±0.2°2θ. In other such embodiments, Form 2 has a PXRD pattern further comprising a peak at the 2θ value of: 16.2°2θ±0.2°2θ.

In another embodiment, lorlatinib maleate hydrate (Form 2) has a PXRD pattern comprising a peak at a 2θ value of: 10.6°2θ±0.2°2θ. In another embodiment, Form 2 has a PXRD pattern comprising a peak at a 2θ value of: 18.5°2θ±0.2°2θ. In another embodiment, Form 2 has a PXRD pattern comprising a peak at a 2θ value of: 27.8°2θ±0.2°2θ. In another embodiment, Form 2 has a PXRD pattern comprising a peak at a 2θ values of: 12.7°2θ±0.2°2θ. In another embodiment, Form 2 has a PXRD pattern comprising a peak at a 2θ value of: 16.2°2θ±0.2°2θ.

In another embodiment, lorlatinib maleate hydrate (Form 2) has a PXRD pattern comprising peaks at 2θ values of: 10.6, 12.7, 18.5 and 27.8°2θ±0.2°2θ. In another embodiment, lorlatinib maleate hydrate (Form 2) has a PXRD pattern comprising peaks at 2θ values of: 10.6, 16.2, 18.5 and 27.8°2θ±0.2°2θ. In yet another embodiment, lorlatinib maleate hydrate (Form 2) has a PXRD pattern comprising peaks at 2θ values of: 10.6, 12.7, 16.2, 18.5 and 27.8°2θ±0.2°2θ. In some such embodiments, the PXRD pattern further comprises one or more additional peaks at 2θ values selected from the group consisting of the peaks in Table 1.

In specific embodiments, lorlatinib maleate hydrate (Form 2) has a PXRD pattern comprising: (a) one, two, three, four, five, or more than five peaks selected from the group consisting of the peaks in Table 1 in °2θ±0.2°2θ; (b) one, two, three, four or five peaks selected from the group consisting of the characteristic peaks in Table 1 in °2θ±0.2°2θ; or (c) peaks at 2θ values essentially the same as shown in FIG. 1.

In one embodiment, lorlatinib maleate hydrate (Form 2) has a Raman spectrum comprising one or more wavenumber (cm$^{-1}$) values selected from the group consisting of: 808, 1307, 1553, 1571, 1672 and 2233 cm$^{-1}$±2 cm$^{-1}$. In another embodiment, lorlatinib maleate hydrate (Form 2) has a Raman spectrum comprising two or more wavenumber (cm$^{-1}$) values selected from the group consisting of: 808, 1307, 1553, 1571, 1672 and 2233 cm$^{-1}$±2 cm$^{-1}$. In another embodiment, lorlatinib maleate hydrate (Form 2) has a Raman spectrum comprising three or more wavenumber (cm$^{-1}$) values selected from the group consisting of: 808, 1307, 1553, 1571, 1672 and 2233 cm$^{-1}$±2 cm$^{-1}$. In another embodiment, lorlatinib maleate hydrate (Form 2) has a Raman spectrum comprising wavenumber (cm$^{-1}$) values of: 808, 1553, 1672 and 2233 cm$^{-1}$±2 cm$^{-1}$. In some such embodiments, Form 2 has a Raman spectrum further comprising a peak at wavenumber (cm$^{-1}$) value of: 1307 cm$^{-1}$±2 cm$^{-1}$. In other such embodiments, Form 2 has a Raman spectrum further comprising a peak at wavenumber (cm$^{-1}$) value of: 1571 cm$^{-1}$±2 cm$^{-1}$. In further such embodiments, Form 2 has a Raman spectrum further comprising peaks at wavenumber (cm$^{-1}$) values of: 1307 and 1571 cm$^{-1}$±2 cm$^{-1}$.

In another embodiment, lorlatinib maleate hydrate (Form 2) has a Raman spectrum comprising a wavenumber (cm$^{-1}$) value of: 808 cm$^{-1}$±2 cm$^{-1}$. In another embodiment, Form 2 has a Raman spectrum comprising a wavenumber (cm$^{-1}$) value of: 1553 cm$^{-1}$±2 cm$^{-1}$. In a further embodiment, Form 2 has a Raman spectrum comprising a wavenumber (cm$^{-1}$) value of: 1672 cm$^{-1}$±2 cm$^{-1}$. In yet another embodiment, Form 2 has a Raman spectrum comprising a wavenumber (cm$^{-1}$) value of: 2233 cm$^{-1}$±2 cm$^{-1}$.

In another embodiment, Form 2 has a Raman spectrum comprising wavenumber (cm$^{-1}$) values of 808, 1307, 1553, 1672 and 2233 cm$^{-1}$±2 cm$^{-1}$. In yet another embodiment, Form 2 has a Raman spectrum comprising wavenumber (cm$^{-1}$) values of: 808, 1553, 1571, 1672 and 2233 cm$^{-1}$±2 cm$^{-1}$. In another embodiment, Form 2 has a Raman spectrum comprising wavenumber (cm$^{-1}$) values of: 808, 1307, 1553, 1571, 1672 and 2233 cm$^{-1}$±2 cm$^{-1}$.

Figure 2:
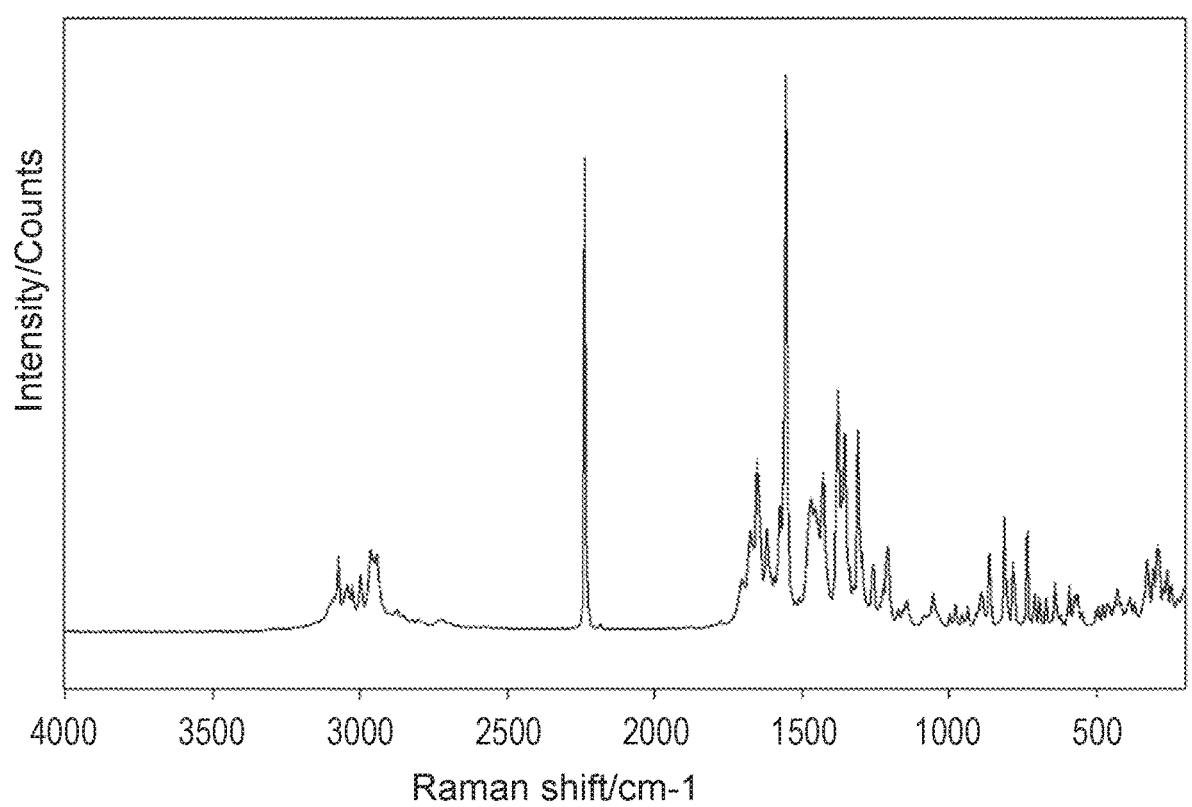
FIG. 2. FT-Raman spectrum of lorlatinib maleate hydrate (Form 2).

In specific embodiments, lorlatinib maleate hydrate (Form 2) has a Raman spectrum comprising: (a) one, two, three, four, five, or more than five wavenumber (cm$^{-1}$) values selected from the group consisting of the values in Table 2 in cm$^{-1}$±2 cm$^{-1}$; (b) one, two, three, four, five, or more than five wavenumber (cm$^{-1}$) values selected from the group consisting of the characteristic values in Table 2 in cm$^{-1}$±2 cm$^{-1}$; or (c) wavenumber (cm$^{-1}$) values essentially the same as shown in FIG. 2.

In one embodiment, lorlatinib maleate hydrate (Form 2) has a $^{13}$C solid state NMR spectrum comprising one or more resonance (ppm) values selected from the group consisting of: 48.7, 116.0, 131.3 and 136.1 ppm±0.2 ppm. In another embodiment, lorlatinib maleate hydrate (Form 2) has a $^{13}$C solid state NMR spectrum comprising two or more resonance (ppm) values selected from the group consisting of: 48.7, 116.0, 131.3 and 136.1 ppm±0.2 ppm. In another embodiment, lorlatinib maleate hydrate (Form 2) has a $^{13}$C solid state NMR spectrum comprising three or more resonance (ppm) values selected from the group consisting of: 48.7, 116.0, 131.3 and 136.1 ppm±0.2 ppm.

In some embodiments, lorlatinib maleate hydrate (Form 2) has a $^{13}$C solid state NMR spectrum comprising the resonance (ppm) value of: 136.1 ppm±0.2 ppm. In another embodiment, Form 2 has a $^{13}$C solid state NMR spectrum comprising the resonance (ppm) value of: 131.3 ppm±0.2 ppm. In another embodiment, Form 2 has a $^{13}$C solid state NMR spectrum comprising the resonance (ppm) values of: 131.3 and 136.1 ppm±0.2 ppm. In some such embodiments, Form 2 has a $^{13}$C solid state NMR spectrum further comprising the resonance (ppm) value of: 48.7 ppm±0.2 ppm. In other such embodiments, Form 2 has a $^{13}$C solid state NMR spectrum further comprising the resonance (ppm) value of: 116.0 ppm±0.2 ppm.

In another embodiment, Form 2 has a $^{13}$C solid state NMR spectrum comprising the resonance (ppm) values of: 48.7, 131.3 and 136.1 ppm±0.2 ppm. In another embodiment, Form 2 has a $^{13}$C solid state NMR spectrum comprising the resonance (ppm) values of: 116.0, 131.3 and 136.1 ppm±0.2 ppm. In another embodiment, Form 2 has a $^{13}$C solid state NMR spectrum comprising the resonance (ppm) values of: 48.7, 116.0, 131.3 and 136.1 ppm±0.2 ppm.

Figure 3:
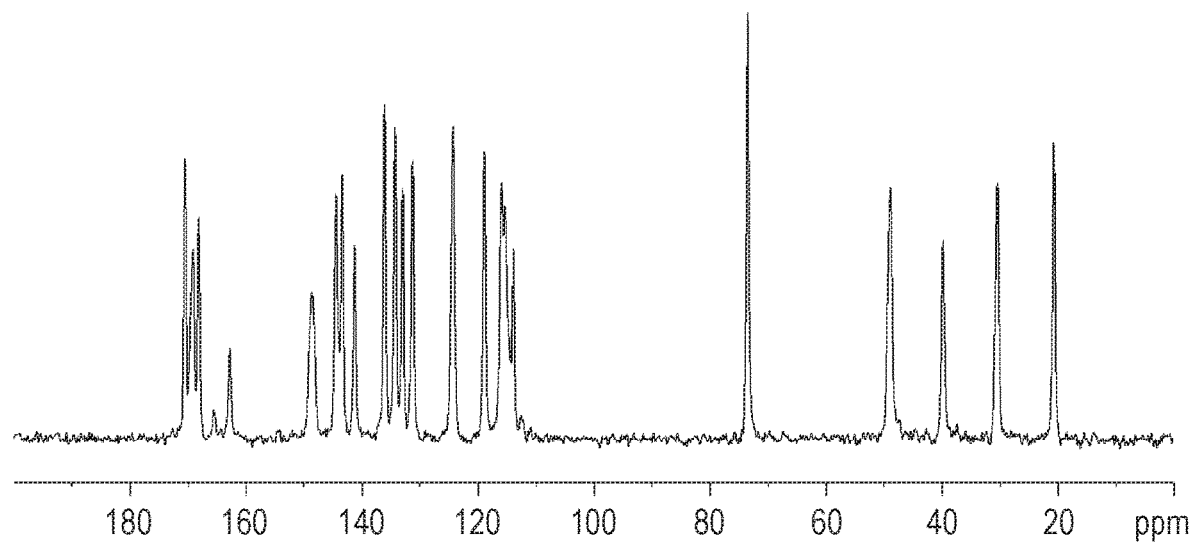
FIG. 3. Carbon CPMAS spectrum of lorlatinib maleate hydrate (Form 2).

In specific embodiments, lorlatinib maleate hydrate (Form 2) has a $^{13}$C solid state NMR spectrum (ppm) comprising: (a) one, two, three, four, five, or more than five resonance (ppm) values selected from the group consisting of the values in Table 3 in ppm±0.2 ppm; (b) one, two, three or four resonance (ppm) values selected from the group consisting of the characteristic values in Table 3 in ppm±0.2 ppm; or (c) resonance (ppm) values essentially the same as shown in FIG. 3.

In another embodiment, lorlatinib maleate hydrate (Form 2) has a $^{19}$F solid state NMR spectrum comprising a resonance (ppm) value of: −110.1 ppm±0.2 ppm.

Figure 4:
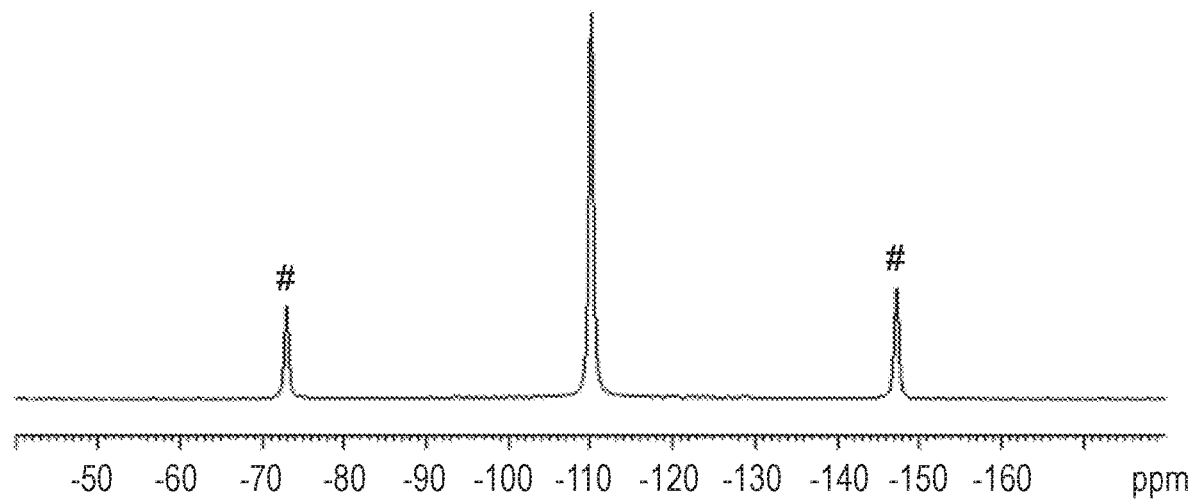
FIG. 4. Fluorine MAS spectrum of lorlatinib maleate hydrate (Form 2).

In another embodiment, Form 2 has a $^{19}$F solid state NMR spectrum (ppm) comprising: (a) the resonance (ppm) value in Table 4 in ppm±0.2 ppm; or (b) resonance (ppm) values essentially the same as shown in FIG. 4.

In further embodiments, lorlatinib maleate hydrate (Form 2) is characterized by a combination of two, three or four of the embodiments described above that are not inconsistent with each other. Exemplary embodiments that may be used to uniquely characterize lorlatinib maleate hydrate (Form 2) are provided below.

In one embodiment, lorlatinib maleate hydrate (Form 2) has a powder X-ray diffraction pattern comprising peaks at 2θ values of: 10.6, 18.5 and 27.8°2θ±0.2°2θ.

In another embodiment, lorlatinib maleate hydrate (Form 2) has a powder X-ray diffraction pattern comprising peaks at 2θ values of: 10.6, 12.7, 18.5 and 27.8°2θ±0.2°2θ.

In another embodiment, lorlatinib maleate hydrate (Form 2) has a powder X-ray diffraction pattern comprising peaks at 2θ value of: 10.6, 16.2, 18.5 and 27.8°2θ±0.2°2θ.

In another embodiment, lorlatinib maleate hydrate (Form 2) has a powder X-ray diffraction pattern comprising peaks at 2θ value of: 10.6, 12.7, 16.2, 18.5 and 27.8°2θ±0.2°2θ.

In a further embodiment, lorlatinib maleate hydrate (Form 2) has: (a) a powder X-ray diffraction pattern comprising peaks at 2θ value of: 10.6, 18.5 and 27.8°2θ±0.2°2θ; and (b) a Raman spectrum comprising wavenumber (cm$^{-1}$) values of: 808, 1553, 1672 and 2233 cm$^{-1}$±2 cm$^{-1}$.

In yet another embodiment, lorlatinib maleate hydrate (Form 2) has: (a) a powder X-ray diffraction pattern comprising peaks at 2θ values of: 10.6, 18.5 and 27.8°2θ±0.2°2θ; and (b) a $^{13}$C solid state NMR spectrum comprising a resonance (ppm) value of: 136.1 ppm±0.2 ppm.

In another embodiment, lorlatinib maleate hydrate (Form 2) has: (a) a powder X-ray diffraction pattern comprising peaks at 2θ values of: 10.6, 18.5 and 27.8°2θ±0.2°2θ; and (b) a $^{19}$F solid state NMR spectrum comprising a resonance (ppm) value of: −110.1 ppm±0.2 ppm.

In another embodiment, lorlatinib maleate hydrate (Form 2) has a Raman spectrum comprising wavenumber (cm$^{-1}$) values of: 808, 1553, 1672 and 2233 cm$^{-1}$±2 cm$^{-1}$.

In another embodiment, lorlatinib maleate hydrate (Form 2) has a Raman spectrum comprising wavenumber (cm$^{-1}$) values of: 808, 1307, 1553, 1672 and 2233 cm$^{-1}$+2 cm$^{-1}$.

In still another embodiment, lorlatinib maleate hydrate (Form 2) has a Raman spectrum comprising wavenumber (cm$^{-1}$) values of: 808, 1553, 1571, 1672 and 2233 cm$^{-1}$±2 cm$^{-1}$.

In yet another embodiment, lorlatinib maleate hydrate (Form 2) has a Raman spectrum comprising wavenumber (cm$^{-1}$) values of: 808, 1307, 1553, 1571, 1672 and 2233 cm$^{-1}$+2 cm$^{-1}$.

In another embodiment, lorlatinib maleate hydrate (Form 2) has: (a) a Raman spectrum comprising wavenumber (cm$^{-1}$) values of: 808, 1553, 1672 and 2233 cm$^{-1}$±2 cm$^{-1}$; and (b) a $^{13}$C solid state NMR spectrum comprising a resonance (ppm) value of: 136.1 ppm±0.2 ppm.

In another embodiment, lorlatinib maleate hydrate (Form 2) has: (a) a Raman spectrum comprising wavenumber (cm$^{-1}$) values of: 808, 1553, 1672 and 2233 cm$^{-1}$±2 cm$^{-1}$; and (b) a $^{19}$F solid state NMR spectrum comprising a resonance (ppm) value of: −110.1 ppm±0.2 ppm.

In another embodiment, lorlatinib maleate hydrate (Form 2) has a $^{13}$C solid state NMR spectrum comprising resonance (ppm) values of: 131.3 and 136.1 ppm±0.2 ppm.

In another embodiment, lorlatinib maleate hydrate (Form 2) has a $^{13}$C solid state NMR spectrum comprising resonance (ppm) values of: 48.7, 131.3 and 136.1 ppm±0.2 ppm.

In yet embodiment, lorlatinib maleate hydrate (Form 2) has a $^{13}$C solid state NMR spectrum comprising resonance (ppm) values of: 116.0, 131.3 and 136.1 ppm±0.2 ppm.

In still another embodiment, lorlatinib maleate hydrate (Form 2) has a $^{13}$C solid state NMR spectrum comprising resonance (ppm) values of: 48.7, 116.0, 131.3 and 136.1 ppm±0.2 ppm.

In another embodiment, lorlatinib maleate hydrate (Form 2) has a $^{19}$F solid state NMR spectrum comprising the resonance (ppm) value of: −110.1 ppm±0.2 ppm.

In another embodiment, lorlatinib maleate hydrate (Form 2) has: (a) a $^{19}$F solid state NMR spectrum comprising the resonance (ppm) value of: −110.1 ppm±0.2 ppm; and (b) a powder X-ray diffraction pattern comprising peaks at 2θ values of: 10.6, 18.5 and 27.8 °2θ±0.2 °2θ.

In another embodiment, lorlatinib maleate hydrate (Form 2) has: (a) a $^{19}$F solid state NMR spectrum comprising the resonance (ppm) value of: −110.1 ppm±0.2 ppm; and (b) a Raman spectrum comprising wavenumber (cm$^{-1}$) values of: 808, 1553, 1672 and 2233 cm$^{-1}$+2 cm$^{-1}$.

In another aspect, the invention provides a pharmaceutical composition comprising lorlatinib maleate hydrate (Form 2) characterized according to any of the embodiments described herein, and a pharmaceutically acceptable carrier or excipient.

In a second aspect, the invention provides anhydrous lorlatinib maleate (Form 1). In one embodiment, anhydrous lorlatinib maleate (Form 1) has a PXRD pattern comprising one or more peaks at 2θ values selected from the group consisting of: 9.8, 12.2, 13.7 and 23.1°2θ±0.2°2θ. In another embodiment, Form 1 has a PXRD pattern comprising two or more peaks at 2θ values selected from the group consisting of: 9.8, 12.2, 13.7 and 23.1°2θ±0.2°2θ In another embodiment, Form 1 has a PXRD pattern comprising three or more peaks at 2θ values selected from the group consisting of: 19.8, 12.2, 13.7 and 23.1°2θ±0.2°2θ.

In another embodiment, Form 1 has a PXRD pattern comprising peaks at 2θ values of: 9.8, 12.2, 13.7 and 23.1°2θ±0.2°2θ. In some such embodiments, Form has a PXRD pattern further comprising one or more additional peaks at the 2θ value in Table 5.

In another embodiment, the invention provides a crystalline form of anhydrous lorlatinib maleate (Form 1), having a $^{19}$F solid state NMR spectrum comprising a resonance (ppm) value of: −104.9 ppm±0.2 ppm.

In another embodiment, Form 1 has a PXRD pattern comprising two or more peaks at 2θ values selected from the group consisting of: 9.8, 12.2, 13.7 and 23.1°2θ±0.2°2θ; and a $^{19}$F solid state NMR spectrum comprising a resonance (ppm) value of: −104.9 ppm±0.2 ppm.

In another embodiment, Form 1 has a PXRD pattern comprising three or more peaks at 2θ values selected from the group consisting of: 9.8, 12.2, 13.7 and 23.1°2θ±0.2°2θ; and a $^{19}$F solid state NMR spectrum comprising a resonance (ppm) value of: −104.9 ppm±0.2 ppm.

In yet another embodiment, Form 1 has a PXRD pattern comprising peaks at 2θ values of: 9.8, 12.2, 13.7 and 23.1°2θ±0.2°2θ; and a $^{19}$F solid state NMR spectrum comprising a resonance (ppm) value of: −104.9 ppm±0.2 ppm.

In some embodiments, Form 1 has a Raman spectrum comprising one, two, three, four, five, or more than five wavenumber (cm$^{-1}$) values selected from the group consisting of: the values in Table 6 in cm$^{-1}$±2 cm$^{-1}$.

In other embodiments, Form 1 has a $^{13}$C solid state NMR spectrum (ppm) comprising: one, two, three, four, five, or more than five resonance (ppm) values selected from the group consisting of the values in Table 7 in ppm±0.2 ppm.

In another aspect, the invention provides a pharmaceutical composition comprising anhydrous lorlatinib maleate (Form 1) characterized according to any of the embodiments described herein, and a pharmaceutically acceptable carrier or excipient.

In another aspect, the invention provides method of treating abnormal cell growth in a mammal, comprising administering to the mammal a therapeutically effective amount of lorlatinib maleate hydrate (Form 2) or anhydrous lorlatinib maleate (Form 1), according to any of the aspects or embodiments described herein.

In another aspect, the invention provides use of lorlatinib maleate hydrate (Form 2) or anhydrous lorlatinib maleate (Form 1), according to any of the aspects or embodiments described herein, in a method of treating abnormal cell growth in a mammal.

In yet another aspect, the invention provides use of lorlatinib maleate hydrate (Form 2) or anhydrous lorlatinib maleate (Form 1), according to any of the aspects or embodiments described herein, in the manufacture of a medicament for treating abnormal cell growth in a mammal.

The term "therapeutically effective amount" as used herein refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

As used herein, "mammal" refers to a human or animal subject. In certain preferred embodiments, the mammal is a human.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous). In frequent embodiments of the methods provided herein, the abnormal cell growth is cancer.

As used herein "cancer" refers to any malignant and/or invasive growth or tumor caused by abnormal cell growth. The term "cancer" includes but is not limited to a primary cancer that originates at a specific site in the body, a metastatic cancer that has spread from the place in which it started to other parts of the body, a recurrence from the original primary cancer after remission and a second primary cancer that is a new primary cancer in a person with a history of previous cancer of different type from latter one.

In some embodiments, the abnormal cell growth is cancer mediated by an anaplastic lymphoma kinase (ALK). In some such embodiments, the ALK is a genetically altered ALK. In other embodiments, the abnormal cell growth is cancer mediated by ROS1 kinase. In some such embodiments, the ROS1 kinase is a genetically altered ROS1 kinase. In frequent embodiments, the abnormal cell growth is cancer, in particular NSCLC. In some such embodiments, the NSCLC is mediated by ALK or ROS1. In specific embodiments, the cancer is NSCLC is mediated by genetically altered ALK or genetically altered ROS1.

Pharmaceutical compositions of the present invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

EXAMPLES

The examples and preparations provided below further illustrate and exemplify particular aspects and embodiments of the invention. It is to be understood that the scope of the present invention is not limited by the scope of the following examples.

General Method 1. Powder X-Ray Diffraction (PXRD)

The PXRD data in FIG. 1 were collected according to the following general protocol.

Instrument Method

PXRD patterns were collected on a Bruker-AXS Ltd. D4 powder X-ray diffractometer fitted with an automatic sample changer, a theta-theta goniometer, automatic beam divergence slit and a PSD Vantec-1 detector. The X-ray tube voltage and amperage were set to 40 kV and 40 mA respectively. The diffractometer was aligned and a calibration check performed using a corundum reference material on the day of data collection. Data was collected at the Cu Kapha1 with wavelength of 1.541 Å using a step size of 0.018 degrees and scan time and 11.3 hours scanning from 2.0 to 65.0 degrees 2-theta for both the active pharmaceutical ingredient (API) and the formulated tablet samples. API samples were prepared by placing the powder in cavity low background holder. The sample powder was pressed by a glass slide to ensure that a proper sample height was achieved and rotated during collection. The tablet samples were subjected to cleaving. The tablet surface was scraped using a scalpel to obtain a smooth and even surface. The tablet was mounted on the PXRD wafer secured with blue tack and covered with x-ray transparent film followed by data collection using the same method as the API sample. Data were collected using Bruker DIFFRAC software and analysis was performed by DIFFRAC EVA software (Version 3.1)

Peak Selection Method

The PXRD patterns collected were imported into Bruker DIFFRAC EVA software, version 3.1. The measured PXRD pattern was aligned to a pattern of a sample with an internal reference to determine the absolute peak positions of the API. The internal reference used was corundum and the absolute peak position for corundum were calculated based on the corundum cell parameters provided in the Certificate of Analysis (NIST SRM 676) for the standard used. All peak of the API were extracted in a table with the accurate peak position provided to one d.p. together with the relative peak intensities.

A typical error of ±0.2°2-theta in peak positions applies to this data. The minor error associated with this measurement can occur as a result of a variety of factors including: (a) sample preparation (e.g., sample height), (b) instrument, (c) calibration, (d) operator (including those errors present when determining the peak locations), and (e) the nature of the material (e.g. preferred orientation and transparency errors). Therefore peaks are considered to have a typical associated error of ±0.2°2-theta. When two peaks, in the list, are considered to overlap (±0.2°2-theta) the less intense peak has been removed from the listing. Peaks existing as shoulders, on a higher intensity adjacent peak, have also been removed from the peak list. While the shoulders may be >0.2°2-theta from the position of the adjacent peak, they are not considered as discernible from the adjacent peak.

General Method 2. Raman Spectroscopy

The Raman spectral data in FIG. 2 were collected according to the following general protocol.

Instrument Method

A Raman spectrum of lorlatinib maleate hydrate (Form 2) was collected using a RAM II FT Raman module attached to a Vertex 70 FTIR spectrometer. The instrument is equipped with a 1064 nm Nd:YAG laser and a liquid nitrogen cooled germanium detector. Prior to data acquisition, instrument performance and calibration verifications were conducted using a white light source and polystyrene and naphthalene references. Raman spectra of a 25 mgA prototype tablet and lorlatinib maleate hydrate (Form 2) were also acquired under the same acquisition conditions.

Samples were analyzed in truncated NMR tubes (5 mm diameter) that were spun during spectral collection. The backscattered Raman signal from the sample in the rotator was optimized and a spectrum was acquired using the following parameters:

Laser power: 500 mW
Spectral resolution: 2 cm$^{-1}$
Collection range: approximately 4000-50 cm$^{-1}$
Number of scans: 512
Apodization function: Blackmann-Harris 4-term The variability in the peak positions in this experimental configuration is within ±2 cm$^{-1}$.

Peak Selection Method

Prior to peak picking the intensity scale of the Stokes scattered Raman signal was normalized to 1.0. Peaks positions were then identified using the peak picking functionality in the GRAMS/AI v.9.1 software (Thermo Fisher Scientific) with the threshold set to 0.05.

Peaks with relative intensities between 1.0 and 0.51, 0.50 and 0.26 and 0.25 or below were labelled as strong, medium and weak respectively.

It is expected that, since FT Raman and dispersive Raman are similar techniques, peak positions reported herein for FT Raman spectra would be consistent with those which would be observed using a dispersive Raman measurement, assuming appropriate instrument calibration.

General Method 3. Solid State NMR (ssNMR) Spectroscopy

The carbon CPMAS and fluorine MAS ssNMR data in FIGS. 3, 4, 7 and 8 were collected according to the following general protocol.

Instrument Method $^{19}$F solid state NMR (ssNMR) analysis was conducted at 20° C. on a Bruker-BioSpin cross-polarization magic angle spinning (CPMAS) probe positioned into a Bruker-BioSpin Avance III HD 400 MHz (1 H frequency) NMR spectrometer. The fluorine ssNMR spectra were collected using a proton decoupled direct polarization magic angle spinning (MAS) experiment. A phase modulated proton decoupling field of approximately 60 kHz was applied during spectral acquisition. The Form 1 spectrum was collected for 8 scans using 20.0 kHz MAS and a recycle delay of 60 seconds. The Form 2 spectrum was collected for 8 scans using 14.0 kHz MAS and a recycle delay of 150 seconds. The fluorine chemical shift scale was referenced using a proton decoupled direct polarization fluorine experiment on an external standard of 50/50 volume/volume of trifluoroacetic acid and water, setting its resonance to −76.54 ppm.

Carbon solid state NMR (ssNMR) analysis on Form 1 was conducted at ambient temperature and pressure on a Varian CPMAS probe positioned into a Varian VNMRS 400 MHz (1 H frequency) NMR spectrometer. The carbon ssNMR spectrum was collected using a CPMAS experiment with TOSS spinning side band suppression. A phase modulated proton decoupling field of approximately 80 kHz was applied during spectral acquisition. The Form 1 spectrum was collected for 5760 scans using 8.0 kHz of MAS, a cross-polarization contact time of 5 ms and a recycle delay of 5 seconds. The carbon chemical shift scale was referenced using a proton decoupled carbon CPMAS experiment on an external standard of crystalline adamantane, setting its downfield resonance to 38.5 ppm (as determined from neat TMS).

Carbon solid state NMR (ssNMR) analysis on Form 2 was conducted at 20° C. on a Bruker-BioSpin CPMAS probe positioned into a Bruker-BioSpin Avance III HD 400 MHz (1 H frequency) NMR spectrometer. The carbon ssNMR spectrum was collected using a proton decoupled CPMAS experiment with TOSS spinning side band suppression. A phase modulated proton decoupling field of approximately 75 kHz was applied during spectral acquisition. The Form 2 spectrum was collected for 5269 scans using 10.0 kHz of MAS, a cross-polarization contact time of 7 ms and a recycle delay of 10.5 seconds. The carbon chemical shift scale was referenced using a proton decoupled carbon CPMAS experiment on an external standard of crystalline adamantane, setting its downfield resonance to 38.5 ppm (as determined from neat TMS).

Peak Selection Method

Automatic peak picking was performed using Bruker-BioSpin TopSpin version 3.2 software. Generally, a threshold value of 5% relative intensity was used to preliminary select peaks. The output of the automated peak picking was visually checked to ensure validity and adjustments were manually made if necessary.

Although specific $^{13}$C and $^{19}$F solid state NMR peak values are reported herein there does exist a range for these peak values due to differences in instruments, samples and sample preparation. This is common practice in the art of solid state NMR because of the variation inherent in peak values. A typical variability for a $^{13}$C and $^{19}$F chemical shift x-axis value is on the order of plus or minus 0.2 ppm for a crystalline solid. The solid state NMR peak heights reported herein are relative intensities. The solid state NMR intensities can vary depending on the actual setup of the experimental parameters and the thermal history of the sample.

The selected characteristic carbon peaks are narrow, have high intensity and belong to single carbon in the molecule. The $^{13}$C and $^{19}$F spectra of Form 2 are presented in FIGS. 3 and 4 respectively.

Example 1

Preparation of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (PF-06463922) Maleate Hydrate (Form 2)

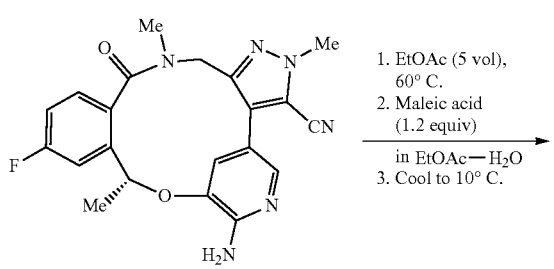

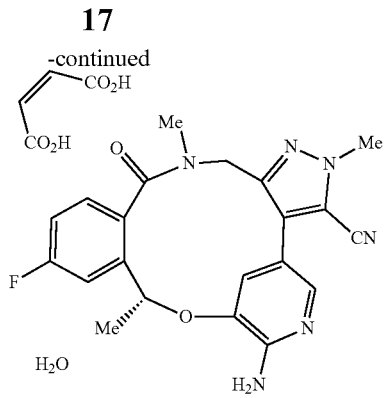

A 500-mL glass jar containing a magnetic stir bar was charged with maleic acid (1.20 equiv., 3.12 g), EtOAc (10.0 mL/g, 90.0 mL) and water (4 equiv., 1.60 mL). The contents were stirred at room temp for several minutes. The clear maleic acid solution was charged to an EasyMax dosing pump.

A 100-mL EasyMax reactor equipped with an overhead agitator, temperature probe and a dosing pump, was charged with lorlatinib free base (9.00 g, 1.00 equiv.) and EtOAc (5.0 mL/g, 45.0 mL) and the suspension was heated to 70° C. (Tj). The reactor was charged with an additional 10 mL of EtOAc (10.0 mL, 1.11 mL/g), to bring the total EtOAc volume to 55.0 mL (6.11 mL/g). Upon visual confirmation that no solids remained and a clear solution was persistent at 70° C., the maleic acid solution was dosed over 90 min (1 mL/min). After 45.0 mL had been dosed, the jacket temperature was decreased to 60° C. and the dosing continued. The reactor was held at 60° (Tj) for 18 h then cooled to 10° C. over 33 min (1.5 K/min).

The solids were isolated by filtration through a 65-mL, medium-porosity, sintered-glass funnel lined with Whatman paper. The mother liquor was returned to the reactor and stirred at 450 rpm to remove the solids that were adhered to the reactor. After several minutes the slurry in the reactor was emptied onto the filter cake. After the mother liquor was pulled from the filter cake, the vacuum was disconnected and fresh, anhydrous EtOAc (15.0 mL) was poured onto the filter cake. The filter cake was agitated manually using a spatula, then the vacuum was reconnected and the EtOAc rinse was pulled away. The product cake was covered with a clean crystallizing dish and dried by pulling air through the filter for 3 days (11.1 g, 92.7% yield).

Characterization of Lorlatinib Maleate Hydrate (Form 2)

PXRD Data

FIG. 1 shows PXRD data for lorlatinib maleate hydrate (Form 2), collected according to General Method 1. A list of PXRD peaks at diffraction angles 2-Theta ° (°2θ)±0.2 °2θ and their relative intensities is provided in Table 1. Characteristic PXRD peaks distinguishing Form 2 are indicated by an asterisk (*).

TABLE 1

| PXRD Peak List for Form 2 (2-Theta °) | |
|---|---|
| Angle °2θ ± 0.2° 2θ | Relative Intensity (%) |
| 6.3 | 3 |
| 7.8 | 3 |

TABLE 1-continued

| PXRD Peak List for Form 2 (2-Theta °) | |
|---|---|
| Angle °2θ ± 0.2° 2θ | Relative Intensity (%) |
| 9.2 | 20 |
| 9.9 | 2 |
| 10.6* | 38 |
| 12.7* | 25 |
| 14.7 | 10 |
| 15.3 | 69 |
| 16.2* | 14 |
| 16.8 | 59 |
| 17.3 | 5 |
| 17.7 | 10 |
| 18.5* | 32 |
| 19.0 | 25 |
| 19.9 | 100 |
| 20.9 | 13 |
| 21.3 | 28 |
| 21.7 | 39 |
| 23.3 | 5 |
| 24.2 | 22 |
| 24.6 | 57 |
| 25.3 | 22 |
| 26.2 | 37 |
| 27.8* | 92 |
| 28.5 | 9 |
| 29.1 | 15 |
| 29.8 | 7 |

FT-Raman Data

FIG. 2 shows the FT-Raman spectrum of lorlatinib maleate hydrate (Form 2), collected according to General Method 2. A list of FT-Raman peaks ($cm^{-1}$) and qualitative intensities is provided in Table 2 in $cm^{-1} \pm 2$ $cm^{-1}$. Characteristic FT-Raman peaks ($cm^{-1}$) peaks distinguishing Form 2 are indicated by an asterisk (*). Normalized peak intensities are indicated as follows: W=weak; M=medium; S=strong.

TABLE 2

| FT Raman Peak List for Form 2 ($cm^{-1}$) | |
|---|---|
| Wave number $cm^{-1} \pm 2$ $cm^{-1}$ | Normalized peak intensity |
| 3069 | w |
| 3040 | w |
| 3022 | w |
| 2992 | w |
| 2960 | w |
| 2939 | w |
| 2233* | s |
| 1672* | w |
| 1648 | m |
| 1616 | w |
| 1571* | w |
| 1553* | s |
| 1468 | w |
| 1454 | w |
| 1427 | w |
| 1377 | m |
| 1352 | m |
| 1307* | m |
| 1295 | w |
| 1256 | w |
| 1207 | w |
| 1051 | w |
| 888 | w |
| 860 | w |
| 808* | w |
| 781 | w |
| 733 | w |
| 638 | w |
| 589 | w |
| 573 | w |
| 562 | w |

TABLE 2-continued

| FT Raman Peak List for Form 2 (cm$^{-1}$) | |
|---|---|
| Wave number cm$^{-1}$ ± 2 cm$^{-1}$ | Normalized peak intensity |
| 326 | w |
| 307 | w |
| 288 | w |
| 257 | w | ssNMR Data

FIG. 3 shows the carbon CPMAS spectrum of lorlatinib maleate hydrate (Form 2), which was collected according to General Method 3. Chemical shifts are expressed in parts per million (ppm) and are referenced to external sample of solid phase adamantane at 29.5 ppm. A list of ssNMR $^{13}$C chemical shifts (ppm) for Form 2 is provided in Table 3 in ppm±0.2 ppm. Characteristic ssNMR $^{13}$C chemical shifts (ppm)distinguishing Form 2 are indicated by an asterisk (*).

TABLE 3

| ssNMR $^{13}$C Chemical Shifts for Form 2 (ppm) | |
|---|---|
| $^{13}$C Chemical Shifts [ppm ± 0.2 ppm] | Relative Intensity (%) |
| 20.6 | 70 |
| 30.3 | 60 |
| 39.7 | 47 |
| 48.7* | 59 |
| 73.4 | 100 |
| 112.6 | 7 |
| 114.0 | 45 |
| 115.4 | 55 |
| 116.0* | 60 |
| 118.9 | 67 |
| 124.3 | 73 |
| 131.3* | 65 |
| 133.0 | 59 |
| 134.3 | 73 |
| 136.1* | 78 |
| 141.3 | 46 |
| 143.4 | 62 |
| 144.5 | 57 |
| 148.6 | 34 |
| 162.7 | 22 |
| 165.4 | 7 |
| 168.1 | 52 |
| 169.1 | 45 |
| 170.4 | 65 |

FIG. 4 shows the fluorine MAS (ssNMR) spectrum of lorlatinib maleate hydrate (Form 2), collected according to General Method 3. Chemical shifts are expressed in parts per million (ppm) referenced to an external sample of trifluoroacetic acid (50% V/V in H$_2$O) at −76.54 ppm.

The ssNMR $^{19}$F chemical shift (ppm) for Form 2 is provided in Table 4 in ppm±0.2 ppm. The characteristic ssNMR $^{19}$F chemical shifts (ppm)distinguishing Form 2 are indicated by an asterisk (*).

TABLE 4

| ssNMR $^{19}$F Chemical Shifts for Form 2 (ppm) | |
|---|---|
| $^{19}$F Chemical Shifts [ppm ± 0.2 ppm] | Relative Intensity (%) |
| −110.1* | 100 |

Example 2

Preparation of Anhydrous (10R)-7-amino-12-fluoro-2,10,16-trimethyl-15-oxo-10,15,16,17-tetrahydro-2H-8,4-(metheno)pyrazolo[4,3-h][2,5,11]benzoxadi-azacyclotetradecine-3-carbonitrile (PF-06463922) Maleate (Form 1)

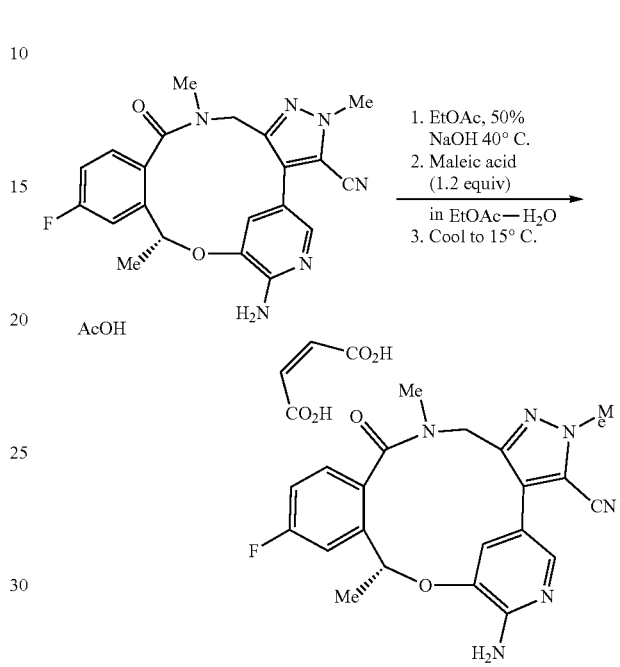

Lorlatinib acetic acid solvate (0.70 kg, 1.5 moles), ethyl acetate (8.5 L) and process water (1.4 L) are combined in a reactor at 15 to 25° C. A 1M solution of sodium hydroxide (1.65 L, 1.65 moles) is charged at a controlled rate over approximately 50 minutes. The reaction mixture was stirred at 15 to 25° C. for at least 15 minutes and then heated to 35-45° C. After reaching 35-45° C., the bottom aqueous layer was separated off and the top organic layer was washed with process water (3.5 L) at 40±5° C. The bottom aqueous wash layer was removed by separation. The product containing organic layer was concentrated by atmospheric distillation to a volume of approximately 3 L volume, treated with ethyl acetate (7 L) and further concentrated to a volume of approximately 4 L solution. The product solution was adjusted to 45 to 55° C. and a solution of maleic acid (0.21 kg, 1.8 moles) dissolved in ethyl acetate (7 L) was charged over 10 to 15 minutes, maintaining the internal temperature between 50±5° C. The mixture was adjusted to 55-65° C. and stirred for approximately 1 hour. The slurry was cooled gradually over at least 1 hour to 10 to 20° C. The product was filtered, washed with ethyl acetate (1.5 L) and then dried under vacuum at 45 to 55° C. A total of 0.638 kg (82% of theory) of anhydrous lorlatinib maleate (Form 1) was recovered.

Characterization of Anhydrous Lorlatinib Maleate (Form 1)

PXRD Data

Figure 5:
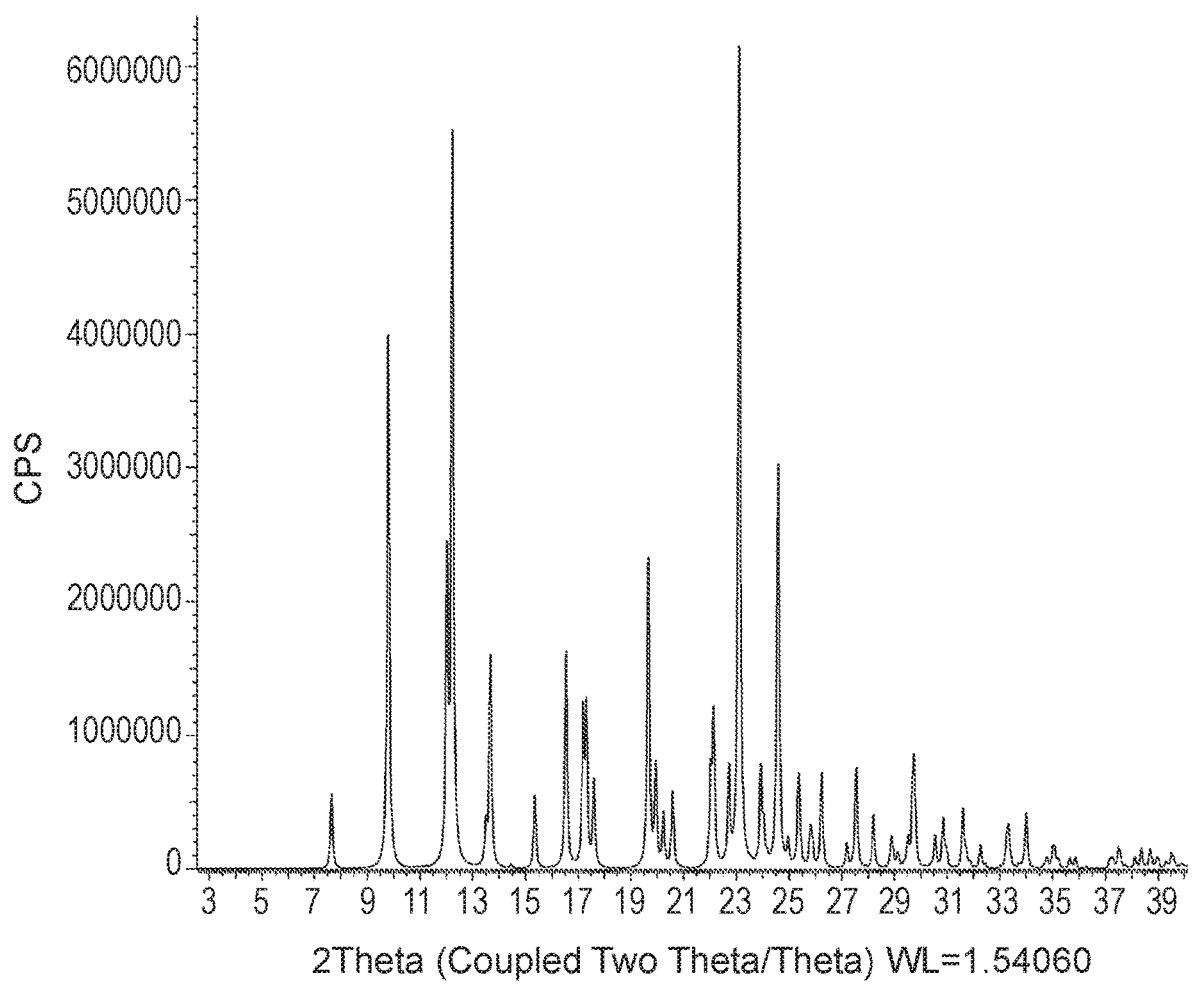
FIG. 5: PXRD pattern of anhydrous lorlatinib maleate (Form 1).

FIG. 5 shows PXRD data for anhydrous lorlatinib maleate (Form 1), collected according to General Method 1. A list of PXRD peaks at diffraction angles 2-Theta ° (°2θ)±0.2°2θ and their relative intensities is provided in Table 5. Characteristic PXRD peaks distinguishing Form 1 are indicated by an asterisk (*).

TABLE 5

PXRD Peak List for Form 1 (2-Theta °)

| Angle °2θ ± 0.2° 2θ | Relative Intensity (%) |
|---|---|
| 7.7 | 9 |
| 9.8* | 65 |
| 12.0 | 40 |
| 12.2* | 90 |
| 13.5 | 6 |
| 13.7* | 26 |
| 15.4 | 9 |
| 19.7 | 38 |
| 19.9 | 13 |
| 20.2 | 7 |
| 20.6 | 9 |
| 22.0 | 13 |
| 22.1 | 19 |
| 22.7 | 12 |
| 23.1* | 100 |
| 23.9 | 13 |
| 24.6 | 49 |

FT-Raman Data

Figure 6:
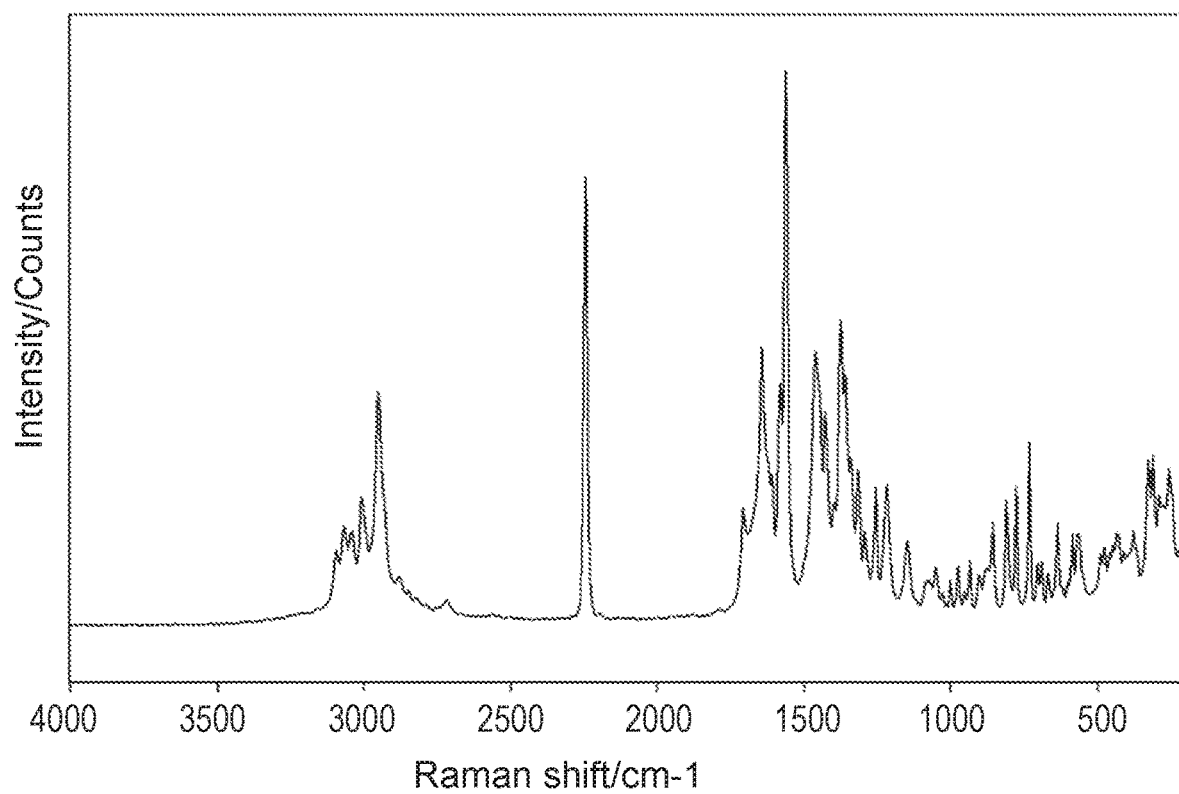
FIG. 6. FT-Raman spectrum of anhydrous lorlatinib maleate (Form 1).

FIG. 6 shows the FT-Raman spectrum of anhydrous lorlatinib maleate (Form 1), collected according to General Method 2. A list of FT-Raman peaks ($cm^{-1}$) and qualitative intensities is provided in Table 6 in $cm^{-1}±2\ cm^{-1}$. Normalized peak intensities are indicated as follows: W=weak; M=medium; S=strong.

TABLE 6

FT Raman Peak List for Form 1 ($cm^{-1}$)

| Wave number $cm^{-1} ± 2\ cm^{-1}$ | Normalized peak intensity |
|---|---|
| 3068 | w |
| 3036 | w |
| 2996 | w |
| 2948 | s |
| 2910 | w |
| 2232 | m |
| 1715 | w |
| 1677 | s |
| 1638 | m |
| 1584 | w |
| 1550 | w |
| 1454 | m |
| 1397 | m |
| 1369 | m |
| 1351 | w |
| 1324 | w |
| 1260 | w |
| 1223 | w |
| 1143 | w |
| 1046 | w |
| 861 | w |
| 811 | w |
| 774 | w |
| 734 | w |
| 695 | w |
| 641 | w |
| 622 | w |
| 561 | w |
| 441 | w |
| 418 | w |
| 322 | w |
| 312 | w |
| 289 | w |
| 261 | w | ssNMR Data

Figure 7:
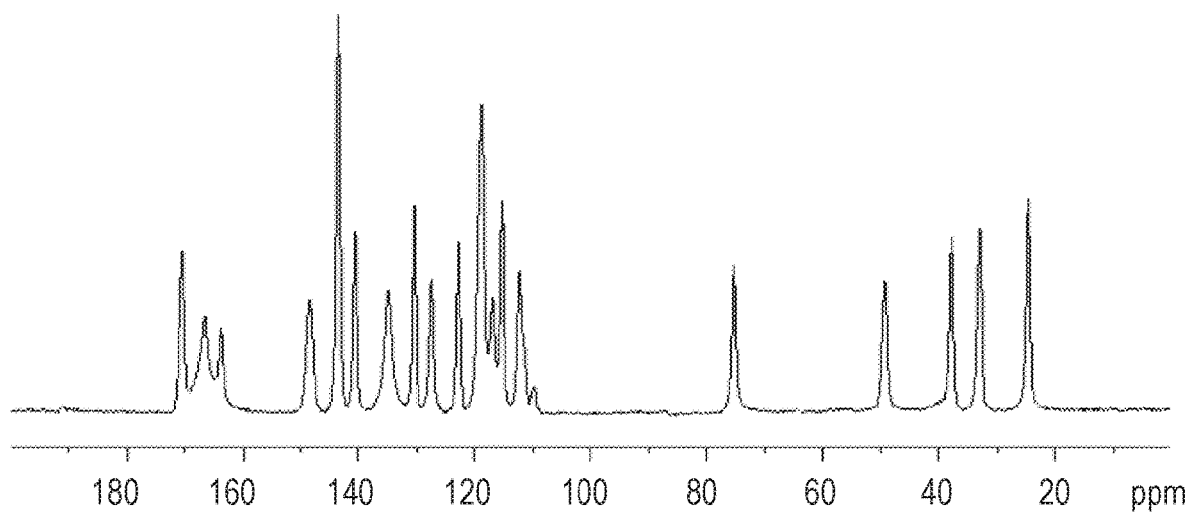
FIG. 7. Carbon CPMAS spectrum of anhydrous lorlatinib maleate (Form 1).

FIG. 7 shows the carbon CPMAS spectrum of anhydrous lorlatinib maleate (Form 1), which was collected according to General Method 3. Chemical shifts are expressed in parts per million (ppm) and are referenced to external sample of solid phase adamantane at 29.5 ppm. A list of ssNMR $^{13}C$ chemical shifts (ppm) for Form 1 is provided in Table 7 in ppm±0.2 ppm.

TABLE 7 ssNMR $^{13}C$ Chemical Shifts for Form 1 (ppm)

| $^{13}C$ Chemical Shifts [ppm ± 0.2 ppm] | Relative Intensity (%) |
|---|---|
| 24.7 | 53 |
| 33.0 | 46 |
| 37.9 | 44 |
| 49.3 | 33 |
| 73.4 | 37 |
| 109.8 | 6 |
| 112.4 | 35 |
| 115.3 | 53 |
| 117.0 | 28 |
| 118.9 | 77 |
| 122.9 | 43 |
| 127.5 | 33 |
| 130.5 | 52 |
| 135.0 | 30 |
| 140.6 | 45 |
| 143.5 | 100 |
| 148.5 | 28 |
| 163.8 | 20 |
| 166.6 | 24 |
| 170.5 | 40 |

Figure 8:
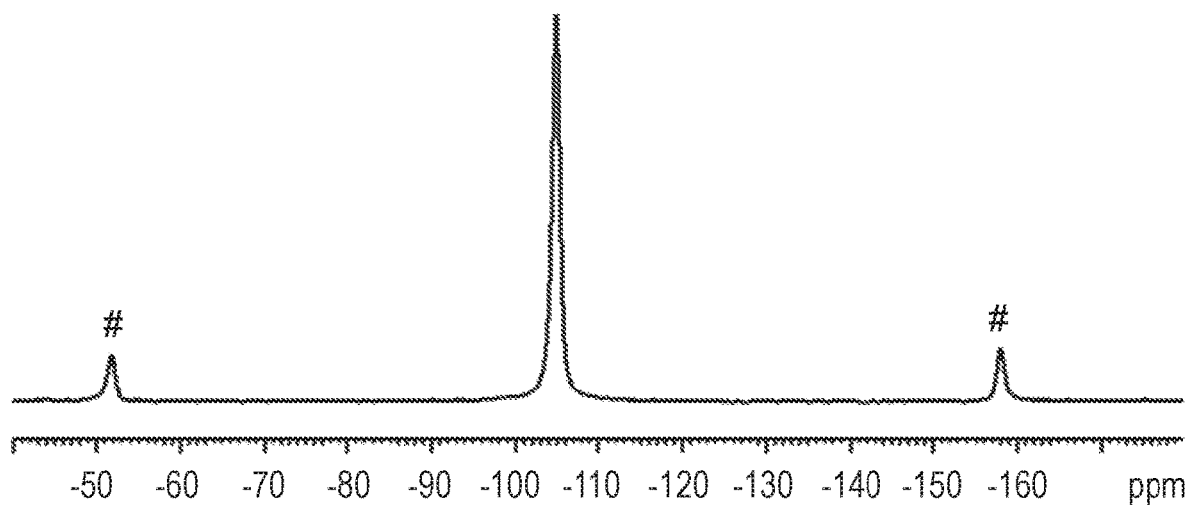
FIG. 8. Fluorine MAS spectrum of anhydrous lorlatinib maleate (Form 1).

FIG. 8 shows the fluorine MAS (ssNMR) spectrum of anhydrous lorlatinib maleate (Form 1), collected according to General Method 3. Chemical shifts are expressed in parts per million (ppm) referenced to an external sample of trifluoroacetic acid (50% V/V in $H_2O$) at −76.54 ppm.

The ssNMR $^{19}F$ chemical shift (ppm) for Form 1 is provided in Table 8 in ppm±0.2 ppm. The characteristic ssNMR $^{19}F$ chemical shift (ppm) distinguishing Form 1 is indicated by an asterisk (*).

TABLE 8 ssNMR $^{19}F$ Chemical Shifts for Form 1 (ppm)

| $^{19}F$ Chemical Shifts [ppm ± 0.2 ppm] | Relative Intensity (%) |
|---|---|
| −104.9* | 100 |

Example 3

Representative Drug Product Formulations of Lorlatinib Maleate Hydrate (Form 2)

Immediate release (IR) tablets comprising lorlatinib maleate hydrate (Form 2) may be prepared using conventional excipients commonly used in tableted formulations. Tablets typically contain from 1-30% of lorlatinib on a w/w basis. Microcrystalline cellulose, dibasic calcium phosphate anhydrous (DCP) and/or lactose hydrate may be used as tablet fillers and sodium starch glycolate may be used as a disintegrant. Magnesium stearate may be used as a lubricant.

A typical IR tablet formulation of Form 2 containing Dibasic Calcium Phosphate Anhydrous (DCP) as a tablet filler (DCP tablet) is provided in Table 9.

TABLE 9

Typical Composition of IR Tablet using DCP as a tablet filler

| | | wt % composition |
|---|---|---|
| Lorlatinib Maleate Hydrate (Form 2) | Active ingredient | 13.33% salt, eq. to 10% active based on 0.75 activity |
| Microcrystalline Cellulose (Avicel PH 102) | Filler | 55.47 |
| Dibasic Calcium Phosphate Anhydrous DCP (A-Tab) | Filler | 27.73 |
| Sodium Starch Glycolate (Explotab) | Disintegrant | 2.60 |
| Magnesium Stearate | Lubricant | 0.87 |
| Total | | 100 |

IR tablets of lorlatinib maleate hydrate (Form 2) may be manufactured using a dry granulation process prior to compression. In this process the crystalline material is blended with some proportion of the excipients falling within standard ranges and the blend is dry granulated using a roller compactor. The granule may be milled as part of this process. The granules are blended with remainder of any of the excipients (e.g., magnesium stearate) prior to compression.

Figure 9:
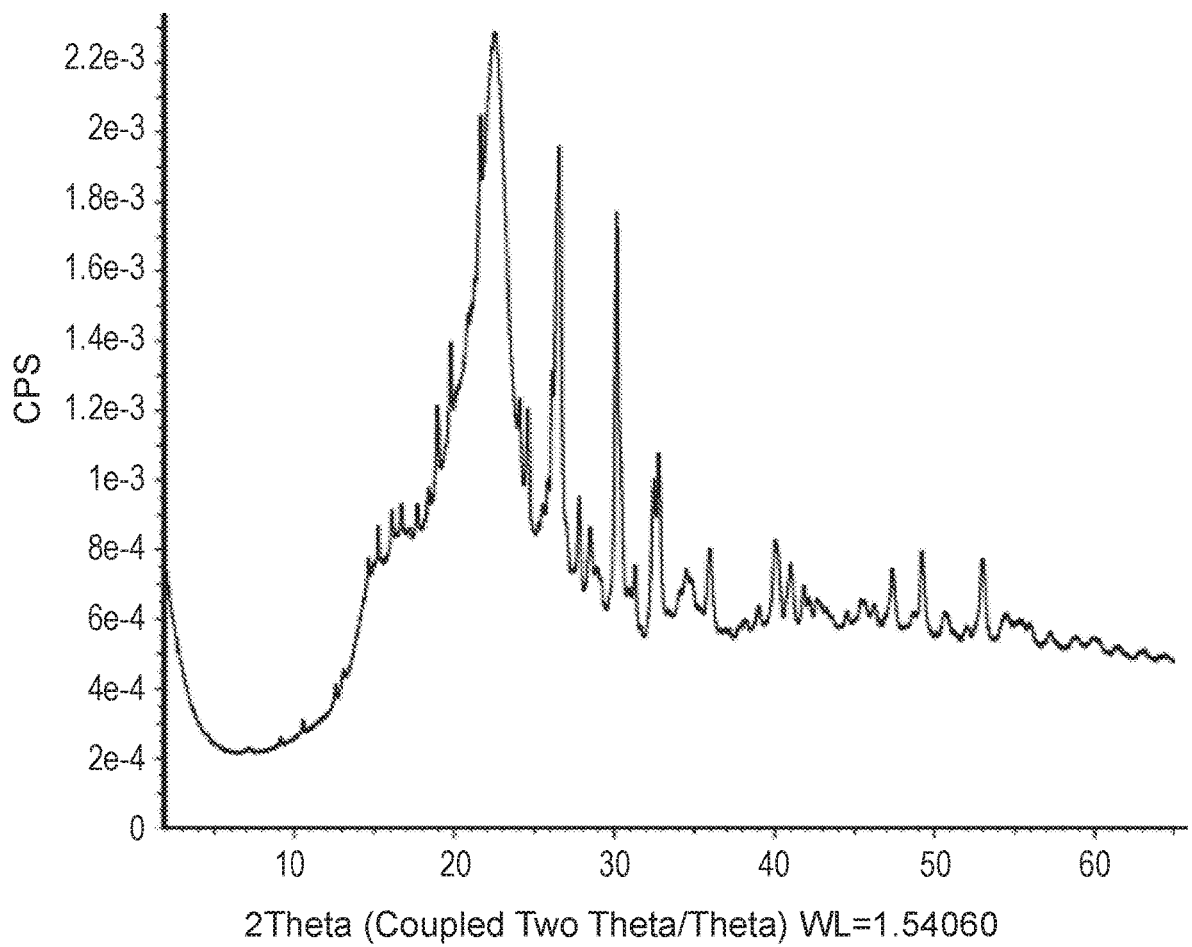
FIG. 9. PXRD pattern of dibasic calcium phosphate anhydrous (DCP) tablet of lorlatinib maleate hydrate (Form 2).
Figure 10:
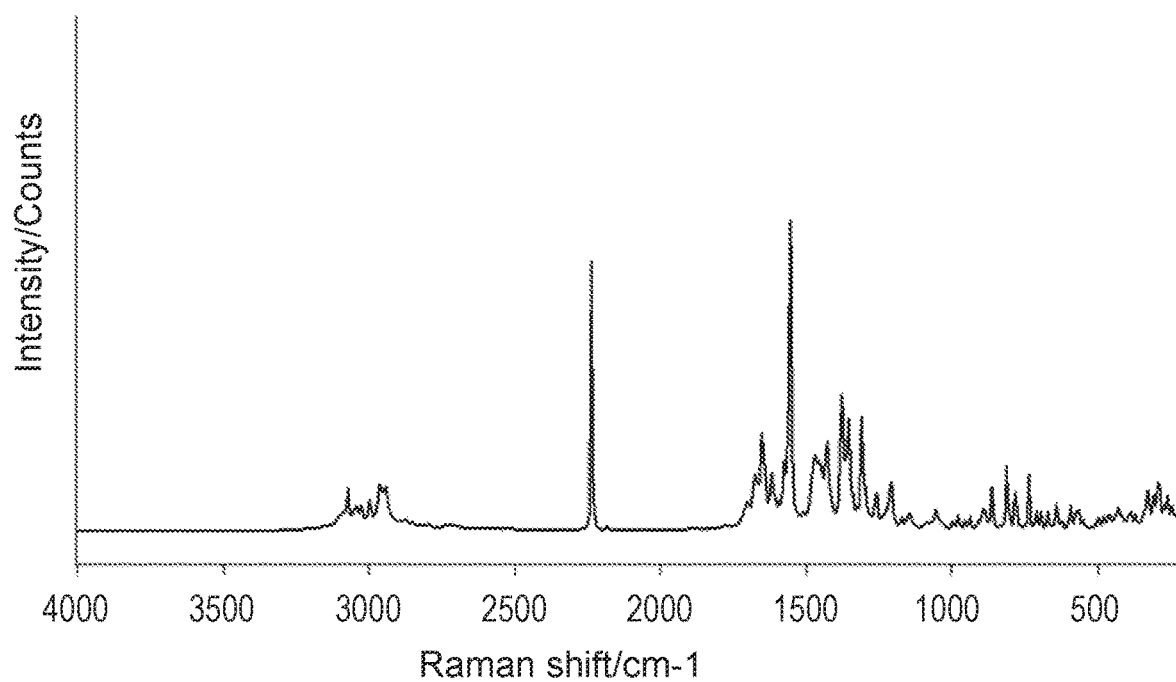
FIG. 10. FT-Raman spectrum of lorlatinib maleate hydrate DCP tablet (Form 2).

FIG. 9 shows the PXRD pattern of a prototype DCP tablet comprising 10% w/w lorlatinib maleate hydrate (Form 2). FIG. 10 show the FT-Raman spectrum of a prototype I DCP tablet comprising 10% w/w lorlatinib maleate hydrate (Form 2).

Example 4

Comparative Thermodynamic Stability

The thermodynamic stability of anhydrous lorlatinib maleate (Form 1) and lorlatinib maleate hydrate (Form 2) was evaluated employing slurry experiments under a range of water activity and temperature conditions. Suspensions of Form 1 were equilibrated for two weeks in acetonitrile/water and methanol/water solvent systems with water activities (Aw) in the range of 0.1 to 0.9, at three different temperatures: 5° C., room temperature and 40° C. After 2 weeks, the solids in equilibrium were isolated and solid form was evaluated by PXRD.

The results summarized in Table 10 demonstrate that anhydrous lorlatinib maleate (Form 1) API converts to the thermodynamically more stable lorlatinib maleate hydrate (Form 2) for water activities in the range of 0.1 to 0.9 and at temperatures from 5° C. to 40° C. Even a minimal amount of water (Aw=0.1) was sufficient to cause conversion of Form 1 to Form 2. Only in anhydrous conditions (Aw=0) was no conversion to the hydrate Form 2 detected. A solvated material was observed in methanol/water at Aw=0.1 and 0.3 and at a temperature of 40° C.

TABLE 10

Slurry Output for anhydrous lorlatinib maleate (Form 1)

| Solvent | Aw/T | 5° C. | RT | 40° C. |
|---|---|---|---|---|
| acetonitrile | 0 | Form 1 | Form 1 | Form 1 |
| acetonitrile/water | 0.1 | Form 2 | Form 2 | Form 2 |
| acetonitrile/water | 0.3 | Form 2 | Form 2 | Form 2 |
| acetonitrile/water | 0.5 | Form 2 | Form 2 | Form 2 |
| acetonitrile/water | 0.75 | Form 2 | Form 2 | Form 2 |
| acetonitrile/water | 0.9 | Form 2 | Form 2 | Form 2 |
| methanol | 0 | Form 1 | Form 1 | Form 1 |
| methanol/water | 0.1 | Form 2 | Form 2 | solvate |
| methanol/water | 0.3 | Form 2 | Form 2 | solvate |
| methanol/water | 0.5 | Form 2 | Form 2 | Form 2 |
| methanol/water | 0.75 | Form 2 | Form 2 | Form 2 |
| methanol/water | 0.9 | Form 2 | Form 2 | Form 2 |

The thermodynamic stability of Form 2 was further assessed in variety of solvent systems at temperatures of 5° C. to 40° C. as shown in Table 11. Suspensions of Form 2 were prepared under the indicated conditions and equilibrated for 2 weeks. Resultant solids were analyzed by PXRD. No conversion to Form 1 was detected under any condition. Formation of new materials in ethanol and methanol is believed to be a solvated form. Form 2 was determined to be thermodynamically stable under a wide range of water activities and solvent conditions.

TABLE 11

Slurry output for lorlatinib maleate hydrate (Form 2)

| Solvents | Aw/T | 5° C. | RT | 40° C. |
|---|---|---|---|---|
| Ethanol | 0 | Form 2 | Form 2 + solvate | solvate |
| MeOAc | 0 | Form 2 | Form 2 | Form 2 |
| 1,4-dioxane | 0 | Form 2 | Form 2 | Form 2 |
| TFE | 0 | Form 2 | Form 2 | amorphous |
| acetonitrile | 0 | Form 2 | Form 2 | Form 2 |
| methanol | 0 | Form 2 | Form 2 + solvate | Form 2 + solvate |
| methanol/water | 0.1 | Form 2 | Form 2 | solvate |
| methanol/water | 0.3 | Form 2 | Form 2 | solvate |
| methanol/water | 0.75 | Form 2 | Form 2 | Form 2 |
| EtOAc | 0 | Form 2 | Form 2 | Form 2 |
| EtOAc/water | 0.1 | Form 2 | Form 2 | Form 2 |
| EtOAc/water | 0.3 | Form 2 | Form 2 | Form 2 |
| EtOAc/water | 0.75 | Form 2 | Form 2 | Form 2 |
| acetone | 0 | Form 2 | Form 2 | Form 2 |
| acetone/water | 0.1 | Form 2 | Form 2 | Form 2 |
| acetone/water | 0.3 | Form 2 | Form 2 | Form 2 |
| acetone/water | 0.75 | Form 2 | Form 2 | Form 2 |
| acetone/water | 0.9 | Form 2 | Form 2 | Form 2 + solvate |

Example 5

Solid-State Physical Stability of Form 1 API and Drug Product

The physical stability of anhydrous lorlatinib maleate (Form 1) API was investigated at a variety of temperatures and percent relative humidities (% RH). Samples were maintained under conditions of 25° C./60% RH and 40° C./75% RH without desiccation and the resulting form was checked via PXRD methods after 3 months. Multiple new PXRD peaks were observed, which were consistent with Form 2. The material stored at 40°/75% RH underwent nearly complete conversion to Form 2 under these conditions based on PXRD. Form 1 stored at ambient temperature and elevated humidity levels of 75% RH and 90% RH underwent full conversion to Form 2 after 6 months.

TABLE 12

Accelerated stability of anhydrous lorlatinib maleate Form 1

| Conditions | Time | Solid Form |
|---|---|---|
| 25° C./60% RH without desiccation | 3 months | Form 1 + Form 2 (major component) |
| 40° C./75% RH without desiccation | 3 months | Form 1 + Form 2 (major component) |
| 75% RH, ambient temperature | 6 months | Form 2 |
| 90% RH, ambient temperature | 6 months | Form 2 |

While anhydrous lorlatinib maleate (Form 1) was metastable with respect to lorlatinib maleate hydrate (Form 2), a representative drug product formulation of Form 1 demonstrated superior physical stability relative to the acetic acid solvate of lorlatinib free base disclosed in WO 2014/207606.

The physical stabilities of Form 1 and lorlatinib acetic acid solvate as drug product were investigated under a variety of conditions. Results are summarized in Table 13. The nature of the solid phase impurity has been studied but not fully characterized.

TABLE 13

Physical stability of Form 1 drug product vs. acetic acid solvate

| Conditions | Time | lorlatinib acetic acid solvate | lorlatinib maleate Form 1 |
|---|---|---|---|
| 70° C./75% RH | 1 week | ~80% impurity | ~10% impurity |
| 50° C./75% RH | 2 weeks | ~30% impurity | ~10% impurity |
| 70° C./40% RH | 2 weeks | ~80% impurity | ~10% impurity |
| 70° C./10% RH | 3 weeks | ~80% impurity | ~10% impurity |

Binary and tertiary mixtures of Form 1 with various excipients were stored at 50° C./75% RH and solid form changes were monitored using PXRD. The mixtures containing stearic acid underwent form changes after 1 week and mixtures containing magnesium stearate showed form changes after 2 weeks.

TABLE 14

Summary of physical stability studies for maleate salt Form 1

| Conditions | Excipients | Time | Output Solid Form |
|---|---|---|---|
| 50° C./75% RH | binary mixture with stearic acid | 1 week | Form 2 |
| 50° C./75% RH | tertiary mixture with stearic acid, lactose | 1 week | Form 2 |
| 50° C./75% RH | tertiary mixture with stearic acid, mannitol | 1 week | Form 2 |
| 50° C./75% RH | binary mixture with magnesium stearate | 2 weeks | Form 1 + Form 2 |
| 50° C./75% RH | tertiary mixture with magnesium stearate and lactose | 2 weeks | Form 1 + Form 2 |
| 50° C./75% RH | tertiary mixture with magnesium stearate, and mannitol | 2 weeks | Form 1 + Form 2 |
| 50° C./75% RH | tablet with lactose, magnesium stearate, Polyplasdone XL | 2 weeks | Form 1 + impurity (~10%) |
| 50° C./75% RH | tablet with DCP, stearic acid, Explotab | 2 weeks | Form 1 |
| 50° C./75% RH | tablet with mannitol, magnesium stearate, Explotab | 2 weeks | Form 1 + impurity (~10%) |
| 50° C./75% RH | tablet with DCP, stearic acid, Polyplasdone XL | 2 weeks | Form 1 |
| 50° C./75% RH | tablet with lactose, stearic acid, Explotab | 2 weeks | Form 1 + impurity (~10%) |
| 50° C./75% RH | tablet with DCP, magnesium stearate, Polyplasdone XL | 2 weeks | Form 1 |
| 50° C./75% RH | tablet with mannitol, stearic acid, Polyplasdone XL | 2 weeks | Form 1 |
| 50° C./75% RH | tablet with DCP, magnesium stearate, Explotab | 2 weeks | Form 1 |

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application and yet these modifications and improvements are within the scope and spirit of the invention.

The invention claimed is:

1. A crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (lorlatinib) maleate hydrate, having a powder X-ray diffraction (PXRD) pattern comprising two or more peaks at 2θ values selected from the group consisting of: 10.6, 12.7, 16.2, 18.5 and 27.8 °2θ±0.2 °2θ.

2. The crystalline form of claim 1, having a PXRD pattern comprising peaks at 2θ values of: 10.6, 18.5 and 27.8 °2θ±0.2 °2θ.

3. The crystalline form of claim 2, having a PXRD pattern further comprising a peak at the 2θ value of: 12.7 °2θ±0.2 °2θ.

4. The crystalline form of claim 2, having a PXRD pattern further comprising a peak at the 2θ value of: 16.2 °2θ±0.2 °2θ.

5. The crystalline form of claim 1, having a Raman spectrum comprising wavenumber ($cm^{-1}$) values of: 808, 1553, 1672 and 2233 $cm^{-1}$±2 $cm^{-1}$.

6. The crystalline form of claim 1, having a $^{13}C$ solid state NMR spectrum comprising resonance (ppm) value of: 136.1 ppm±0.2 ppm.

7. The crystalline form of claim 1, having a $^{19}F$ solid state NMR spectrum comprising resonance (ppm) value of: −110.1 ppm±0.2 ppm.

8. A crystalline form of lorlatinib maleate hydrate, having a Raman spectrum comprising two or more wavenumber ($cm^{-1}$) values selected from the group consisting of: 808, 1307, 1553, 1571, 1672 and 2233 $cm^{-1}$±2 $cm^{-1}$.

9. The crystalline form of claim 8, having a Raman spectrum comprising wavenumber ($cm^{-1}$) values of: 808, 1553, 1672 and 2233 $cm^{-1}$±2 $cm^{-1}$.

10. The crystalline form of claim 9, having a Raman spectrum further comprising the wavenumber ($cm^{-1}$) value of: 1307 $cm^{-1}$±2 $cm^{-1}$.

11. The crystalline form of claim 9 or 10, having a Raman spectrum further comprising the wavenumber ($cm^{-1}$) value of: 1571 $cm^{-1}$±2 $cm^{-1}$.

12. The crystalline form of claim 8, having a $^{13}C$ solid state NMR spectrum comprising resonance (ppm) value of: 136.1 ppm±0.2 ppm.

13. The crystalline form of claim 8, having a $^{19}$F solid state NMR spectrum comprising a resonance (ppm) value of: −110.1 ppm±0.2 ppm.

14. A crystalline form of lorlatinib maleate hydrate, having a $^{13}$C solid state NMR spectrum comprising two or more resonance (ppm) values selected from the group consisting of: 48.7, 116.0, 131.3 and 136.1 ppm±0.2 ppm.

15. The crystalline form of claim 14, having a $^{13}$C solid state NMR spectrum comprising resonance (ppm) values of: 131.3 and 136.1 ppm±0.2 ppm.

16. The crystalline form of claim 15, having a $^{13}$C solid state NMR spectrum further comprising the resonance (ppm) value of: 48.7 ppm±0.2 ppm.

17. The crystalline form of claim 15, having a $^{13}$C solid state NMR spectrum further comprising the resonance (ppm) value of: 116.0 ppm±0.2 ppm.

18. A crystalline form of lorlatinib maleate hydrate, having a $^{19}$F solid state NMR spectrum comprising a resonance (ppm) value of: −110.1 ppm±0.2 ppm.

19. The crystalline form of claim 18, having a PXRD pattern comprising peaks at 2θ values of: 10.6, 18.5 and 27.8 °2θ±0.2 °2θ.

20. The crystalline form of claim 18, having a Raman spectrum comprising wavenumber (cm$^{-1}$) values of: 808, 1553, 1672 and 2233 cm$^{-1}$±2 cm$^{-1}$.

21. A pharmaceutical composition comprising the crystalline form of lorlatinib maleate hydrate according to claim 1, and a pharmaceutically acceptable carrier or excipient.

\* \* \* \* \*